(12) United States Patent
Chiu et al.

(10) Patent No.: US 11,609,232 B2
(45) Date of Patent: Mar. 21, 2023

(54) METHOD AND DEVICE OF USING AQUEOUS TWO-PHASE SYSTEMS (ATPS) FOR ENHANCING DIAGNOSTICS FOR SEXUALLY TRANSMITTED INFECTIONS

(71) Applicant: PHASE DIAGNOSTICS, INC., Garden Grove, CA (US)

(72) Inventors: Yin To Chiu, Irvine, CA (US); Garrett Lee Mosley, Anaheim, CA (US); Brian Sangwoo Lee, La Mirada, CA (US)

(73) Assignee: PHASE DIAGNOSTICS, INC., Garden Grove, CA (US)

( * ) Notice: Subject to any disclaimer, the term of this patent is extended or adjusted under 35 U.S.C. 154(b) by 406 days.

(21) Appl. No.: 16/642,910

(22) PCT Filed: Aug. 30, 2018

(86) PCT No.: PCT/US2018/048822
§ 371 (c)(1),
(2) Date: Feb. 28, 2020

(87) PCT Pub. No.: WO2019/046563
PCT Pub. Date: Mar. 7, 2019

(65) Prior Publication Data
US 2020/0348303 A1 Nov. 5, 2020

Related U.S. Application Data

(60) Provisional application No. 62/553,207, filed on Sep. 1, 2017.

(51) Int. Cl.
| | | |
|---|---|---|
| C12Q 1/00 | (2006.01) | |
| G01N 33/571 | (2006.01) | |
| G01N 1/34 | (2006.01) | |
| G01N 1/40 | (2006.01) | |
| G01N 33/543 | (2006.01) | |

(52) U.S. Cl.
CPC ............ *G01N 33/571* (2013.01); *G01N 1/34* (2013.01); *G01N 1/4005* (2013.01); *G01N 33/543* (2013.01); *G01N 2333/16* (2013.01); *G01N 2333/295* (2013.01)

(58) Field of Classification Search
CPC .................................................. G01N 33/571
See application file for complete search history.

(56) References Cited

U.S. PATENT DOCUMENTS

| | | | |
|---|---|---|---|
| 6,132,763 | A | 10/2000 | Fisher |
| 6,399,385 | B1 | 6/2002 | Croyle et al. |
| 7,626,017 | B2 | 12/2009 | Laugharn, Jr. et al. |
| 7,666,583 | B2 | 2/2010 | Mor et al. |
| 7,803,405 | B2 | 9/2010 | Keating et al. |
| 9,823,247 | B2 | 11/2017 | Kamei et al. |
| 10,006,911 | B2 | 6/2018 | Kamei et al. |
| 10,359,423 | B2 | 7/2019 | Kamei et al. |
| 10,578,616 | B2 | 3/2020 | Kamei et al. |
| 11,287,426 | B2 | 3/2022 | Kamei et al. |
| 11,327,075 | B2 | 5/2022 | Kamei et al. |
| 2002/0042506 | A1 | 4/2002 | Kristyanne et al. |
| 2005/0077497 | A1 | 4/2005 | Anderson |
| 2006/0025579 | A1 | 2/2006 | Riedl et al. |
| 2006/0166349 | A1 | 7/2006 | Kepka et al. |
| 2007/0161000 | A1 | 7/2007 | Van Alstine et al. |
| 2008/0242825 | A1 | 10/2008 | Devi et al. |
| 2009/0192111 | A1 | 7/2009 | Bader et al. |
| 2009/0286966 | A1 | 11/2009 | Christensen et al. |
| 2010/0174052 | A1 | 7/2010 | Hjorth et al. |
| 2010/0179252 | A1 | 7/2010 | Johansson et al. |
| 2011/0257378 | A1 | 10/2011 | Tran et al. |
| 2011/0263040 | A1 | 10/2011 | Jones |
| 2013/0164825 | A1 | 6/2013 | Gabriele et al. |
| 2014/0221549 | A1 | 8/2014 | Bodkhe et al. |
| 2014/0227712 | A1 | 8/2014 | Horlitz et al. |
| 2014/0228549 | A1 | 8/2014 | Bernhard et al. |
| 2015/0253320 | A1 | 9/2015 | Kamei et al. |

(Continued)

FOREIGN PATENT DOCUMENTS

| | | | |
|---|---|---|---|
| CN | 101679481 | A | 3/2010 |
| CN | 102272144 | A | 12/2011 |

(Continued)

OTHER PUBLICATIONS

Luechau, Frank; et al. (2009) Primary capture of high molecular weight nucleic acids using aqueous two-phase systems. Separation and purification technology, 66.1: 202-207.

Nazer, Behzad; et al. (2017) Plasmid DNA affinity partitioning using polyethylene glycol-sodium sulfate aqueous two-phase systems. Journal of Chromatography B, 1044: 112-119.

Sorber L, et al. (2017) A Comparison of Cell-Free DNA Isolation Kits: Isolation and Quantification of Cell-Free DNA in Plasma. J Mol Diagn. Jan;19(1):162-168.

Frank Luechau, et al., Partition of plasmid DNA in polymer-salt aqueous two-phase systems, Separation and Purification Technology, Apr. 20, 2009, pp. 397-404, vol. 66, No. 2, Elsevier Science, Amsterdam, NL.

(Continued)

*Primary Examiner* — Albert M Navarro
(74) *Attorney, Agent, or Firm* — Eagle IP Limited

(57) ABSTRACT

This invention relates to a method and device for improving the accuracy and performance of detecting or diagnosing sexually transmitted infections (STIs) or STI-causing pathogens. In one embodiment, the present method and device are related to removing one or more interfering molecules such as urea from urine sample, where these interfering molecules alter the performance of Lateral-Flow Immunoassay (LFA). In one embodiment, an aqueous two-phase system (ATPS) embedded entirely within a porous material allows spontaneous phase separation and the target STI-causing pathogens is concentrated in one of the separated phases. In one embodiment, a detection module such as the Lateral-Flow Immunoassay (LFA) is used in connection with other modules so as to detect or diagnose the sexually transmitted infections or the pathogens associated with STIs with an improved performance.

21 Claims, 8 Drawing Sheets

(56) References Cited

U.S. PATENT DOCUMENTS

| | | | |
|---|---|---|---|
| 2018/0100854 | A1 | 4/2018 | Kamei et al. |
| 2018/0259521 | A1 | 9/2018 | Kamei et al. |
| 2019/0033308 | A1 | 1/2019 | Kamei et al. |
| 2019/0187140 | A1 | 6/2019 | Kamei et al. |
| 2019/0250156 | A1 | 8/2019 | Kamei et al. |
| 2019/0391143 | A1 | 12/2019 | Kamei et al. |
| 2020/0150116 | A1 | 5/2020 | Kamei et al. |
| 2020/0284791 | A1 | 9/2020 | Kamei et al. |
| 2022/0252598 | A1 | 8/2022 | Kamei et al. |

FOREIGN PATENT DOCUMENTS

| | | | |
|---|---|---|---|
| CN | 102421898 | A | 4/2012 |
| CN | 106662582 | A | 5/2017 |
| CN | 110003323 | A | 7/2019 |
| EP | 0268946 | A2 | 6/1988 |
| JP | 2000245460 | A | 9/2000 |
| JP | 2002537106 | A | 11/2002 |
| JP | 2007525222 | A | 9/2007 |
| JP | 2017513015 | A | 5/2017 |
| NO | 2017214315 | A1 | 12/2017 |
| WO | 0050161 | A1 | 8/2000 |
| WO | 2002057289 | A1 | 7/2002 |
| WO | 2011159537 | A2 | 12/2011 |
| WO | 2014128129 | A1 | 8/2014 |
| WO | 2015134938 | A1 | 9/2015 |
| WO | 2016155888 | A1 | 10/2016 |
| WO | 2017041030 | A1 | 3/2017 |
| WO | 2018039139 | A1 | 3/2018 |
| WO | 2018183454 | A1 | 10/2018 |
| WO | 2018183465 | A1 | 10/2018 |
| WO | 2018222972 | A1 | 12/2018 |
| WO | 2019046553 | A1 | 3/2019 |
| WO | 2019046563 | A1 | 3/2019 |
| WO | 2019055926 | A2 | 3/2019 |
| WO | 2019118712 | A1 | 6/2019 |
| WO | 2019143895 | A1 | 7/2019 |
| WO | 2019143943 | A2 | 7/2019 |
| WO | 2019144016 | A1 | 7/2019 |
| WO | 2019144030 | A1 | 7/2019 |

OTHER PUBLICATIONS

Vijayaragavan K. Saagar et al., Separation of porcine parvovirus from bovine serum albumin using PEG-salt aqueous two-phase system, Journal of Chromatography B, Sep. 1, 2014, pp. 118-126, vol. 967, NL.
Erik Jue et al., Using an aqueous two-phase polymer-salt system to rapidly concentrate viruses for improving the detection limit of the lateral-flow immunoassay: Concentrating Viruses in a Polymer-Salt System, Biotechnology and Bioengineering, Dec. 1, 2014, pp. 2499-2507, vol. 111, No. 12, US.
Paz Sean et al., A simplified SARS-CoV-2 detection protocol for research laboratories, Plos One, Dec. 18, 2020, p. e0244271, vol. 15, No. 12.
Ziegler YS, et al. (2014) Plasma membrane proteomics of human breast cancer cell lines identifies potential targets for breast cancer diagnosis and treatment. PLoS One. 9(7):e102341.
Schindler J, et al. (2008) Aqueous polymer two-phase systems for the proteomic analysis of plasma membranes from minute brain samples. J Proteome Res 7(1):432-442.
Spindler KL, et al. (2015) Circulating free DNA as biomarker and source for mutation detection in metastatic colorectal cancer. PLoS One.10(4):e0108247.
Riedl W, et al. (2008) Membrane-supported extraction of biomolecules with aqueous two-phase systems[J]. Desalination, 224(1-3): 160-167.
Frerix A, et al. (2005) Scalable recovery of plasmid DNA based on aqueous two-phase separation. Biotechnol Appl Biochem. 42(Pt 1):57-66.
Crucho Cic, et al. (2017) Polymeric nanoparticles: A study on the preparation variables and characterization methods. Mater Sci Eng C Mater Biol Appl. 80:771-784.
Shin H, et al. (2015) High-yield isolation of extracellular vesicles using aqueous two-phase system. Sci Rep. 5:13103.
Zeringer E, et al. (2015) Strategies for isolation of exosomes. Cold Spring Harb Protoc. (4):319-323.
Iqbal M, et al. (2016) Aqueous two-phase system (ATPS): an overview and advances in its applications. Biol Proced Online. 18:18.
Zhou et al. (2015) Nanoparticle Vesicles with Controllable Surface Topographies through Block Copolymer-Mediated Self-Assembly of Silica Nanospheres, Langmuir, vol. 31(48), 11 pp. 13214-13220.

Bashir et al. (2016) Controlled-release of Bacillus thurigiensis formulations encapsulated in light-resistant colloidosomal micro-capsules for the management of lepidopteran pests of *Brassica* crops, Peerj., vol. 4(e2524). pp. 1-14.

Sigma-Aldrich "Poly(ethylene glycol) octyl ether" Retrieved from the Internet <URL:https://www.google.com/search?q=poly%28ethylene+glycol%29+octyl+ether&source=Int&tbs=cdr%3A1%2Ccd_min%3A%2Ccd_max%3A1%2F18%2F2018&tbm=> <URL https://www.sigmaaldrich.com/catalog/product/sigma/40530?lang=en®ion=US> [retrieved on Jun. 16, 2020].

Steven B. Zimmerman and Lizabeth D. Murphy, Excluded Volume Effects on the Partition of Single- and Double-Stranded Oligodeoxynucleotides Between Two Liquid Phases, Biopolymers, Oct. 1992, 1365-1373, vol. 32, Issue 10, John Wiley & Sons, Inc.

Steven B. Zimmerman and Stefan O. Trach, Excluded Volume Effects on the Partition of Macromolecules Between Two Liquid Phases, Biopolymers, 1990, 703-718, vol. 30, Issue 7-8, John Wiley & Sons, Inc.

T.Matos, et. al., Isolation of PCR DNA fragments using aqueous two-phase systems, Separation and Purification Technology, Feb. 10, 2014, 144-148, vol. 122, Elsevier B.V.

Andreas Frerix, et. al., Exploitation of the Coil-Globule Plasmid DNA Transition Induced by Small Changes in Temperature, pH Salt, and Poly(ethylene glycol) Compositions for Directed Partitioning in Aqueous Two-Phase Systems, Langmuir, Mar. 25, 2006, 4282-4290, vol. 22 Issue 9, American Chemical Society.

Ricky Y. T. Chiu, et al., An Aqueous Two-Phase System for the Concentration and Extraction of Proteins from the Interface for Detection Using the Lateral-Flow Immunoassay, PLOS One, Nov. 10, 2015, 1-14, PLOS, California, US.

K. Jessie, et al., Protein Precipitation Method for Salivary Proteinsand Rehydration Buffer for Two-Dimensional Electrophoresis, Biotechnology, 2008, 686-693, 7 (4), Asian Network for Scientific Information.

Richard J. Wicks, et al., The extraction and purification of DNA labelled with [methyl-3 H]thymidine in aquatic bacterial production studies, Journal of Plankton Research, 1987, 1159-1166, vol. 9 No. 6, IRL Press Limited, Oxford, England.

Donald C Rio, et al., Purification of RNA by SDS solubilization and phenol extraction, Cold Spring Harb Protoc, Jun. 2010, 1-4, vol. 2010 Issue 6, Cold Spring Harbor Laboratory Press, NY, USA.

Zsolt Czimmerer, et al., A Versatile Method to Design Stem-Loop Primer-Based Quantitative PCR Assays for Detecting Small Regulatory RNA Molecules, PLOS One, Jan. 31, 2013, 1-10, vol. 8 Issue 1, PLOS, California, US.

METHOD AND DEVICE OF USING AQUEOUS TWO-PHASE SYSTEMS (ATPS) FOR ENHANCING DIAGNOSTICS FOR SEXUALLY TRANSMITTED INFECTIONS

CROSS-REFERENCE TO RELATED APPLICATIONS

This application claims the benefit of U.S. Provisional Application No. 62/553,207, filed Sep. 1, 2017. The entire contents and disclosures of the preceding application are incorporated by reference into this application.

Throughout this application, various publications are cited. The disclosures of these publications in their entireties are hereby incorporated by reference into this application to more fully describe the state of the art to which this invention pertains.

STATEMENT REGARDING FEDERALLY SPONSORED RESEARCH OR DEVELOPMENT

This invention was made at least in part with government support under National Institutes of Health (NIH). The United States Government may have certain rights in the invention.

FIELD OF THE INVENTION

This invention relates to a method and device to improve the detection accuracy and performance for diagnosing sexually transmitted infections by improving the sensitivity of the Lateral-Flow Immunoassay (LFA). The present method and device are related to removing one or more interfering molecules present in a sample that alter the LFA response using aqueous two-phase system (ATPS) embedded entirely within a porous material, allowing spontaneous phase separation and concentration, for detection using the Lateral-Flow Immunoassay (LFA). The performance can be further optimized by using 3D paper well or porous paper with tapered shape.

BACKGROUND OF THE INVENTION

Chlamydia, caused by infection with *Chlamydia trachomatis* (CT), is the most prevalent sexually transmitted infection in the United States. However, the current standard for CT testing is unable to provide results within one patient visit, resulting in many missed opportunities to treat infected patients in time. Furthermore, current rapid tests are grossly inadequate with sensitivities under 50%. Key opinion leaders and healthcare providers in major testing locations (such as physicians' offices, sexually transmitted infections (STI) clinics, and campus health centers) have strongly affirmed that the highly ineffective testing protocol is one of the largest factors fueling the STI epidemic. Simple and effective testing protocol with satisfying accuracy is therefore highly desired.

Lateral flow assay (LFA) is one of the popular detection tools widely used in in detecting bacteria since it is rapid and easy to use. LFA is a simple dipstick test that is inexpensive to perform and can be used on various samples, such as urine. However, LFA tests are generally only capable of providing qualitative results rather than not quantitative results, due to their intrinsic limit of detection. In addition, LFA on urine sample is always not sensitive enough for diagnostic test due to the interfering molecules such as urea that alter the LFA detection response. Such interfering molecules have a negative impact on the accuracy, precision, and robustness of the method. An improved method and device to improve the limit of detection of LFA are thus very important.

To overcome these limitations, the present invention provides an improved method and device to lower the detection limit of LFA by removing one or more interfering molecules such as urea from urine samples prior to detection and concentrating the target STI-causing pathogens such as *Chlamydia trachomatis* on aqueous two-phase system (ATPS) embedded entirely within a porous material for concentrating the pathogens. The resulting sample is then subject to further analysis by lateral flow assay (LFA). The above can be easily and quickly done in one or two steps without complex equipment. The present method and device can improve the detection limit of LFA up to 100× or more.

The method and device described herein can improve the accuracy, sensitivity and efficiency of the detection and quantification of STD-causing pathogens and therefore are capable of improving the performance of various analytical or diagnostic technologies relying on the detection and/or quantification of these STD-causing pathogens. Many related diseases can be cured if the diseases are detected early.

SUMMARY OF THE INVENTION

The present invention relates to a method and device for improving the accuracy and performance of detecting or diagnosing sexually transmitted infections (STIs) or STI-causing pathogens.

In one embodiment, the present method and device are related to removing one or more interfering molecules such as urea directly from urine sample in advance of the detection of the STI.

In one embodiment, the present method and device are related to an aqueous two-phase system (ATPS) embedded entirely within a porous material, which allows spontaneous phase separation and concentration of target molecules in a sample, in couple with a detection using the Lateral-Flow Immunoassay (LFA).

In one embodiment, the present invention utilizes an aqueous two-phase system (ATPS) to achieve a one-step diagnosis. In another embodiment, gold nanoparticles, urine-based lateral flow assay (LFA) test, and/or optimized three-dimensional (3D) paper well/porous paper with tapered shape and other components are integrated with the present ATPS to enhance the performance of the one-step diagnostic device described herein.

In one embodiment, the present invention provides an improved method and device capable of lowering the detection limit of LFA by removing one or more interfering molecules such as urea from a urine sample and concentrating sexually-transmitting infection-causing pathogens such as *Chlamydia trachomatis* and Human Immunodeficiency Virus (HIV) on an aqueous two-phase system (ATPS) embedded entirely within a porous material prior to detection by LFA. Sample resulting from the concentration is then subject to further analysis by a lateral flow assay (LFA) for detecting the presence of the target pathogen or sexually transmitted infection.

In one embodiment, the present method and device can improve the detection limit of LFA up to 100× or more.

BRIEF DESCRIPTION OF THE DRAWINGS

FIG. 1B shows the target molecule (shown in darker colour) concentrated in the bottom phase with a 9:1 volume ratio.

DETAILED DESCRIPTION OF THE INVENTION

In the following description, several embodiments of the invention are described. For purposes of explanation, specific configurations and details are set forth in order to provide a thorough understanding of the embodiments. In addition, to the plural or singular forms of a word and to the extent that orientations of the embodiments are described as, "top", "bottom", "front", "back", "left", "right" and the like, these wordings are to aid the reader in understanding the embodiments and are not meant to be limiting physically. It is apparent to a person skilled in the art that the present invention may be practiced without specific details. The invention will be better understood by reference to the examples which follow, but those skilled in the art will readily appreciate that the specific examples are for illustrative purposes only and should not limit the scope of the invention which is defined by the claims which follow thereafter. It is to be noted that the transitional term "comprising" or "including", which is synonymous with "containing" or "characterized by", is inclusive or open-ended and does not exclude additional, unrecited elements or method steps.

The present invention relates to a method and device for improving the accuracy and performance of detecting or diagnosing sexually transmitted infections (STIs) or STI-causing pathogens by improving the sensitivity of the Lateral-Flow Immunoassay (LFA).

In one embodiment, the present method and device are related to removing one or more interfering molecules such as urea directly from urine sample in advance of the detection of the STI.

In one embodiment, the present method and device are related an aqueous two-phase system (ATPS) embedded entirely within a porous material, which allows spontaneous phase separation and concentration of target molecules in a sample, in couple with a detection using the Lateral-Flow Immunoassay (LFA).

In one embodiment, the present invention utilizes an aqueous two-phase system (ATPS) to achieve a one-step diagnosis. In another embodiment, gold nanoparticles, urine-based lateral flow assay (LFA) test, and/or optimized three-dimensional (3D) paper/other components are integrated with the present ATPS to enhance the performance of the present one-step diagnostic device.

Figure 3:
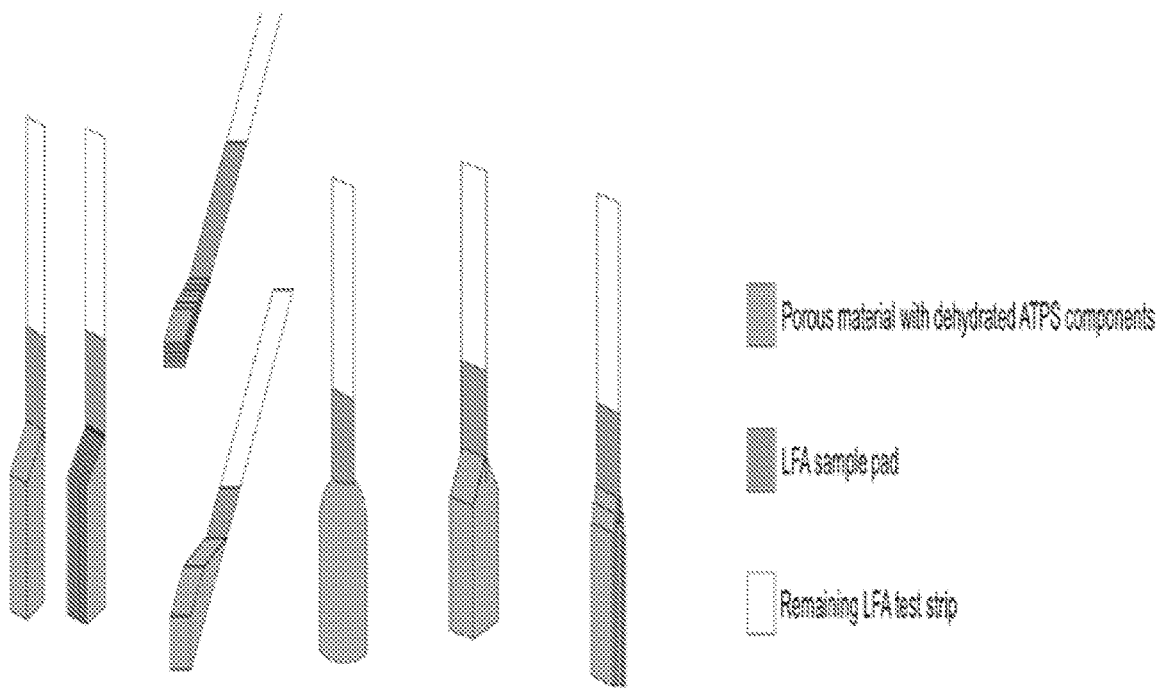
FIG. 3 shows various examples of 3D paper well with dehydrated ATPS components according to some embodiments of the present invention.

In one embodiment, the present 3D paper well includes but is not limited to the following structures: "point up" by cutting one side of the porous material at 45-degree, "pointing" by stacking layers of porous material of different lengths, cylindrical shape with various dimensions of radius and height, "arrow" by cutting the porous material on each of the two opposite sides at 45-degree, "arrow" by stacking layers of porous material of different lengths for each of the two opposite sides. In one embodiment, the present 3D paper takes any form of structures as illustrated in FIG. 3.

In one embodiment, the present invention provides an improved method and device capable of lowering the detection limit of LFA by removing one or more interfering molecules such as urea from a urine sample and concentrating sexually-transmitting infection-causing pathogens such as *Chlamydia trachomatis* and Human Immunodeficiency Virus (HIV) on an aqueous two-phase system (ATPS)

embedded entirely within a porous material prior to detection by LFA. Sample resulting from the concentration is then subject to further analysis by a lateral flow assay (LFA) for detecting the presence of the target pathogen or sexually transmitted infection. In one embodiment, the above can be easily and quickly done in one or two steps without complex equipment or specialized training.

In one embodiment, the present method and device can improve the detection limit of LFA up to 100× or more.

In one embodiment, the present invention provides a one-step method and device for detecting or diagnosing STIs.

In one embodiment, the present invention further provides a handheld device incorporated with the one-step system described herein, which possesses at least the following characteristics: (1) Fast: Results can be delivered to the patient in less than 10 minutes; (2) Affordable: As low as $15 retail price; (3) Accurate: Sensitivity and specificity approaching lab-based assays; (4) Convenient: Handheld and can be used at any time without equipment or special training. Therefore, it is expected to obtain Clinical Laboratory Improvement Amendments of 1988 (CLIA) waived status, which is the lowest complexity for clinical tests and over-the-counter (OTC) status. With this unique combination of attributes that is unmatched by any competing product, the present invention has immense potential to revolutionize healthcare for many people around the world.

Type of Samples and Target Pathogen or Bacterial

This invention relates to a method and device for improving the accuracy and performance of detecting or diagnosing sexually transmitted infections (STIs) or STI-causing pathogens by improving the sensitivity of the Lateral-Flow Immunoassay (LFA).

In one embodiment, the present method and device improves the accuracy and performance of detecting or diagnosing infection caused by *Chlamydia trachomatis* in a subject by detecting *Chlamydia trachomatis* bacteria present in the subject's sample. In one embodiment, the present method and device improves the accuracy and performance of detecting *Chlamydia trachomatis* in a subject sample. In one embodiment, the sample is a urine sample. In one embodiment, the sample is a genital swab. In one embodiment, the sample is a throat swab. In one embodiment, the sample is a saliva sample. In one embodiment, the sample is a whole blood sample. In one embodiment, the sample is a dried blood spot. In one embodiment, the sample is a plasma sample.

Urine is a liquid by-product of metabolism in humans and in many animals. Human urine is yellowish in color. The pH normally is within the range of 5.5 to 7 with an average of 6.2. Urine contains proteins, urea and other substances that are useful for medical therapy and are ingredients in many prescription drugs. Human urine consists primarily of water (91% to 96%), with organic solutes including urea, creatinine, uric acid, and trace amounts of enzymes, carbohydrates, hormones, fatty acids, pigments, and mucins, and inorganic ions such as sodium ($Na^+$), potassium ($K^+$), chloride ($Cl^-$), magnesium ($Mg^{2+}$), calcium ($Ca^{2+}$), ammonium ($NH_4^+$), sulfates ($SO_4^{2-}$), and phosphates (e.g., $PO_4^{3-}$). The presence of significant levels of protein or sugar in urine indicates potential health concerns.

In one embodiment, the present invention is used to detect pathogens including virus and bacteria that cause sexually transmitted infections in human or animals.

In one embodiment, the STI-causing pathogens to be detected by the present invention include, but are not limited to, *Chlamydia trachomatis* (CT), *Neisseria gonorrhoeae*, *Trichomonas vaginalis* and *Treponema pallidum* (syphilis) and Human Immunodeficiency Virus (HIV).

Removing Molecules Interfering with Detection of Target Molecules

In one embodiment, this invention provides methods and devices for improving the accuracy and performance of detecting or diagnosing sexually transmitted infections (STIs) by improving the sensitivity of the Lateral-Flow Immunoassay (LFA) for such detection or diagnosis. In one embodiment, the present method and device improve the sensitivity of LFA by removing impurities that interfere with the detection from the sample. In one embodiment, the interfering impurity is urea and the present invention remove urea from a urine sample prior to the detection and thereby improves the performance of the detection.

It is well known in the art that urea can denature protein and urea is the key element in urine. In this invention, it is surprising that urea in the urine has adverse effects to the sensitivity of LFA when it is used to detect the presence of STI-causing pathogens obtained from a urine sample. In a general LFA detection module for pathogen detection, antibody used is a Y shape protein. The shape is critical to antibody in order to recognize a unique pathogen having corresponding antigen(s). The antibody binds to a specific antigen where their interaction is similar to a lock and key. Specific and effective binding between the antibody and target antigen is critical to the sensitivity and specificity of the detection and also the detection limit. Unfortunately, the inventors of this invention observed that urea in urine interferes with the LFA detection by changing the binding site of antibodies and affect the correct and effective binding with the target antigen on the target pathogen. As a result, the amount of actual target antigen captured by antibodies is significantly lowered and the detection result will be far lower than expected. False negative and hence delayed treatment may be resulted due to poor detection.

In the present invention, one or more of the interfering molecules especially urea in urine samples are first removed from the urine sample, thereby significantly improve the sensitivity of LFA detection by permitting a specific and effective binding between antibodies and target antigen in the course of LFA detection. In one embodiment, the detection limit of LFA module is enhanced by at least 100-fold when the purifying module and the concentration module are used in conjunction with LFA as described in this invention.

There are various methods available to remove urea from urine. Most of them involved the use of organic solvent which may kill or affect the activity of target pathogen or configuration of the target antigen to be detected. In one embodiment, citric acid was found to be the most suitable purifying reagent for removing urea in this invention. Citric acid is a weak acid which does not affect the bioactivity of STI-causing pathogens or their antigens subject to subsequent detection. In one embodiment, the following procedures are followed: Urine is mixed with citric acid (25% w/v in water) in 1:1, the mixture is vortexed to mix thoroughly and allowed to precipitate for 5 min at room temperature. This is followed by centrifugation at 15,000 rpm, for 2 min. The supernatant was collected. Sodium carbonate was added for neutralization until pH is about 6.2. The supernatant can then be concentrated by lyophilizer or ATPS system as described herein (e.g. FIGS. 1A and 1B) if needed.

It is surprised that the addition of citric acid causes precipitation of proteins in urine as well as acidification of the urine sample. By removing molecules interfering with downstream detection, the present invention enhances the performance of downstream detection and analysis.

In one embodiment, the concentration of citric acid is in the range of about 0.01% to about 50% weight by volume concentration. In various embodiments, the citric acid solution is selected from a citric acid solution that is about 1% w/v, about 2% w/v, about 3% w/v, about 4% w/v, about 5% w/v, about 6% w/v, about 7% w/v, about 8% w/v, about 9% w/v, about 10% w/v, about 11% w/v, about 12% w/v, about 13% w/v, about 14% w/v, about 15% w/v, about 16% w/v, about 17% w/v, about 18% w/v, about 19% w/v, about 20% w/v, about 21% w/v, about 22% w/v, about 23% w/v, about 24% w/v, about 25% w/v, about 26% w/v, about 27% w/v, about 28% w/v, about 29% w/v, about 30% w/v, about 31% w/v, about 32% w/v, about 33% w/v, about 34% w/v, about 35% w/v, about 36% w/v, about 37% w/v, about 38% w/v, about 39% w/v, about 40% w/v, about 41% w/v, about 42% w/v, about 43% w/v, about 44% w/v, about 45% w/v, about 46% w/v, about 47% w/v, about 48% w/v, about 49% w/v, and about 50% w/v.

In one embodiment, the molar ratios of urea in the urine sample to citric acid added is in the range of from 2:1 to 1:2. Preferably, the molar ratio of urea in the urine sample to citric acid added into sample is 1:1.

In one embodiment, the purifying agent is selected from the group consisting of lactic acid, acetic acid, and activated carbon.

Three-Dimensional (3D) Paper Well and One-Step ATPS-LFA Device

In one embodiment, the present invention provides a three-dimensional paper well for introducing a sample to the detection device.

In one embodiment, the present invention provides an ATPS-LFA device for detecting a STI-causing pathogen or diagnosing a STI, comprising a sample application pad (such as the 3D paper well described herein), a conjugate pad, a detection pad and an absorbent pad.

Figure 9:
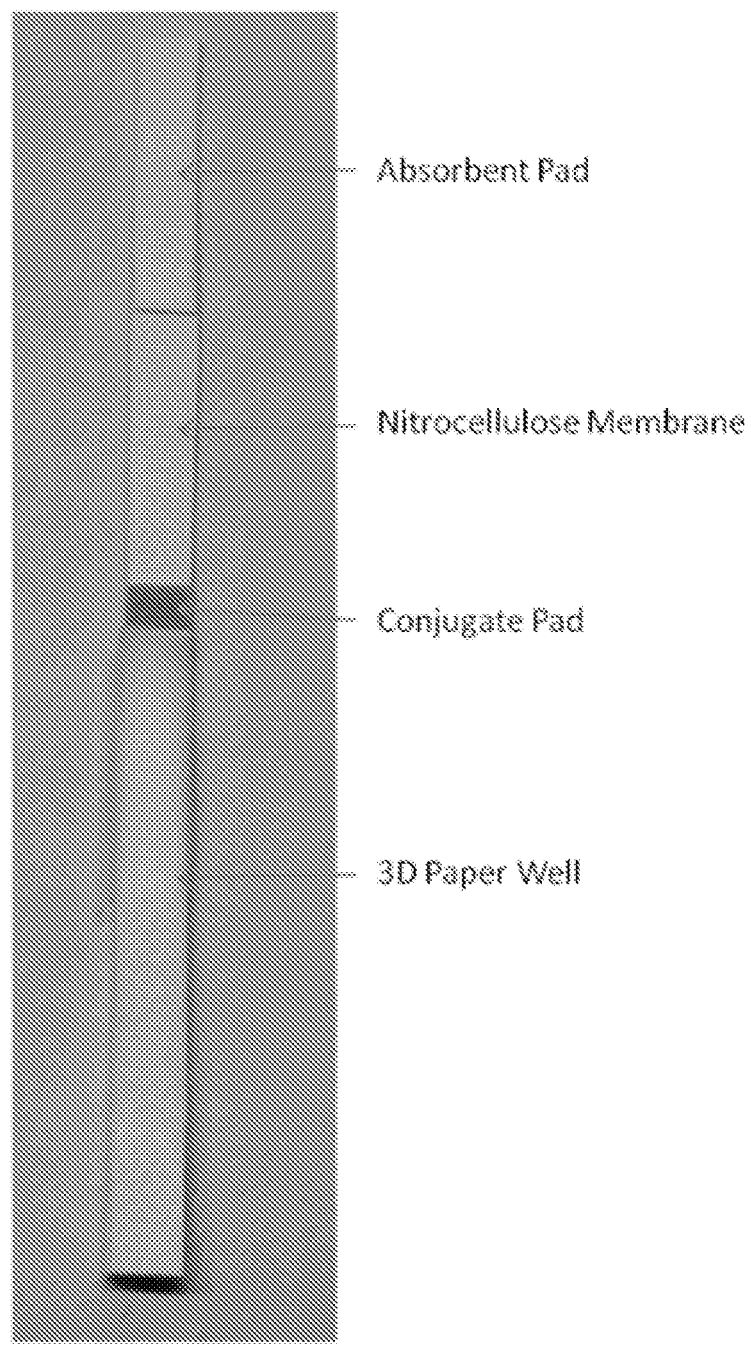
FIG. 9 shows a one-step device by incorporating dehydrated ATPS components with an LFA test strip according to one embodiment of the present invention. The 3D paper well is being held together with the LFA test strip by tape.

In one embodiment, the present device takes the form of a test strip which comprises: a sample application pad (or a 3D paper well), a conjugate pad, a nitrocellulose membrane and an adsorbent pad. One or more test and control lines are covered on the nitrocellulose membrane. In one embodiment, the present device takes the form as depicted in FIG. 9. In one embodiment, the concentration of the target analyte is conducted on the sample application pad. In one embodiment, the concentration is separately conducted on a concentrating module.

In one embodiment, the sample application pad (3D paper well) is made of porous material (e.g. fiber glass paper) embedded with ATPS for concentrating target molecules in the sample. In one embodiment, paper pieces can be stack together to form a 3D paper well (e.g. those as shown in FIG. 3) to increase the cross-sectional area so as to further enhance the concentration.

In one embodiment, the porous material has regions with a tapered shape or structure and regions without a tapered shape or structure. In one embodiment, the regions of the porous material with a tapered shape or structure have a greater cross-sectional area normal the direction of flow upstream and a smaller cross-sectional area normal the direction of flow downstream.

In one embodiment, the specific tapered shape or structure of the porous material is selected to increase aqueous two-phase domain coalescence. By funneling the fluid flow to a point, it is possible to reduce the change of the domain separating from each other. Therefore, they are more likely to interact with each other which is required for the domain to coalescence.

In one embodiment, the specific tapered shape or structure of the porous material is selected to increase the volume of the leading fluid phase. By increasing the amount of domains that coalescence with each other, it is possible to create a larger leading fluid phase and may be beneficial for downstream applications of the device.

In one embodiment, the specific tapered shape or structure of the porous material is selected to reduce and/or eliminate fracturing and/or separation of the leading fluid phase. By funneling the fluid flow to a point, it is possible to reduce the change of the domain separating from each other.

In one embodiment, the specific tapered shape or structure of the porous material is selected to increase macroscopic phase separation.

In one embodiment, the specific tapered shape or structure of the porous material is selected to increase target partitioning between the first phase and the second phase. By funneling the fluid flow to a point, it is possible to reduce the change of the domain separating from each other. Therefore, the domains will be closer to each other which makes it easier for the target analytes to partition between the domains because there is a smaller distance for them to diffuse before they reach the proper domain.

In one embodiment, sample (either crude, partially or fully purified) is applied on the application pad to start the assay. Fluids and hence molecules therein present in one region of the device can migrate to another region of the device as they travel along the device. As such, target and non-target molecules in the sample can interact with other components on the device (e.g. ATPS components and conjugated antibodies pre-deposited in the device) as they flow through the device. Sample pad should be capable of migrating fluid in a smooth, continuous and homogenous manner. In one embodiment, sample application pad is provided to concentrate the target analyte before its transportation by embedded ATPS on the porous material.

In one embodiment, conjugate pad is provided on which labeled biorecognition molecules are dispensed. In one embodiment, material of conjugate pad which immediately releases the labeled conjugate upon contact with the moving liquid sample is chosen. Labeled conjugate should stay stable over the entire life span of lateral flow strip. Any variations in dispensing, drying or release of conjugate can change results of assay significantly. Poor preparation of labeled conjugate can adversely affect the sensitivity of assay. The properties of conjugate pad material have an effect on the release of labeled conjugate and sensitivity of the assay. In one embodiment, glass fiber, cellulose, polyesters and other materials known in the art that is compatible with LFA are used to make conjugate pad for LFA. In one embodiment, colloidal gold nanoparticles which acts as colorimetric indicators for the target antigen is provided.

In one embodiment, the labeled biorecognition molecule comprises a biorecognition molecule and a label. In one embodiment, the biorecognition molecule includes but is not limited to antibodies, aptamers, and molecular beacons.

In one embodiment, the label includes but is not limited to gold nanoparticles, colored latex beads, magnetic particles, carbon nanoparticles, selenium nanoparticles, silver nanoparticles, quantum dots, up converting phosphors, organic fluorophores, textile dyes, enzymes, liposomes and others. In one embodiment, any material that is used as a label should be detectable at very low concentrations and it should retain its properties upon conjugation with biorecognition molecules. This conjugation is also expected not to change features of biorecognition probes.

Nitrocellulose membrane is highly critical in determining the sensitivity of LFA. Nitrocellulose membranes are available in different grades. In one embodiment, test and control lines are drawn over the membrane to report the test result (test line) and verify the validity of the test (control line). So an ideal membrane should provide support and good binding to capture probes (e.g. antibodies). Nonspecific adsorption over test and control lines may affect results of the assay significantly, thus a good membrane will be characterized by lesser nonspecific adsorption in the regions of test and control lines. Wicking rate of nitrocellulose membrane can also influence assay sensitivity. Generally, nitrocellulose membranes are easy to use, inexpensive, and offer high affinity for proteins and other biomolecules. Proper dispensing of bioreagents, drying and blocking of the membrane also play a role in improving sensitivity of assay.

In one embodiment, the biorecognition molecules is one of the following classes of immune globulin: IgG, IgM, IgA, IgD, IgE and secretory IgA. In one embodiment, the biorecognition molecules are preferably selected from the group consisting of IgG, IgA and IgM classes.

In one embodiment, labeled biorecognition molecules are immobilized at conjugate pad. In one embodiment, a primary antibody or aptamer against target analyte is immobilized over test line. In one embodiment, a secondary antibody or probe against labeled biorecognition molecules is immobilized at control zone.

In one embodiment, after sample containing an analyte migrates to conjugate pad, the analyte is captured by the immobilized labeled antibody or aptamer conjugate and results in the formation of labeled antibody conjugate/analyte complex. At test line, label antibody conjugate/analyte complex is captured by another antibody which is primary to the analyte. Analyte becomes sandwiched between labeled and primary antibodies forming labeled antibody conjugate/analyte/primary antibody complex. Excess labeled antibody conjugate will be captured at control zone by secondary antibody.

In one embodiment, absence of color at test line is an indication for the presence of analyte while appearance of color both at test and control lines indicates a negative result.

In one embodiment, adsorbent pad works as sink at the end of the ATPS-LFA device. It also helps in maintaining flow rate of the liquid over the membrane and prevent the sample from flowing back to the direction of the application pad. Adsorbent capacity to hold liquid can play an important role in results of assay.

ATPS (Aqueous Two-Phase System)

Similar to an oil-water system, an ATPS consists of two distinct liquid phases, the ratios of which can easily be controlled. Biomolecules suspended in the ATPS system partition into one of the two aqueous phases based on their physicochemical properties (e.g., hydrophilicity) resulting in concentration. Based on an established proof-of-concept device which leveraged the ATPS concentration step in conjunction with a conventional lateral-flow immunoassay (LFA), the subject invention demonstrates a significantly lowered limit of detection in a simple medium than Quidel's QuickVue, which is the current FDA-approved rapid test predicate based on LFA.

In the present invention, ATPS adapted to urine (a physiologically relevant complex medium), which is essential to testing in a clinical or home setting. Data provided in the invention demonstrated that the present invention (detection using ATPS in conjugation with LFA) is able to detect *Chlamydia trachomatis* in urine sample with a lowered limit of detection as compared to LFA alone or QuickVue. A true one-step ATPS-LFA test is also provided, whereby all components of the ATPS are fully integrated into the paper microfluidic strip, precluding the need for liquid handling except for the initial step of sample collection. The present invention achieves a significantly improved sensitivity in detecting CT and other STI-causing pathogens. A head-to-head comparison using remnant clinical urine samples demonstrated that the performance of the present invention is better than the FDA-approved QuickVue test.

The advantage of the invention is that high purity and concentration of the target pathogen or bacterial can be obtained in a simple way and compatible with downstream application using Lateral-Flow Immunoassay (LFA) without further steps of purification or concentration.

The methods and devices provided herein are robust, inexpensive, simple, easy to handle, safe, user friendly and fast. The present method is able to purify and concentrate the target pathogen or bacterial and thereby ensures the performance of the downstream applications using the purified and concentrated pathogens will not be affected by impurities in the original sample.

Because of the unique features described herein, the present invention can purify and concentrate target pathogen conveniently and rapidly without the use of complex instrumentation, and is applicable to samples containing the target pathogen in a very low amount, or of a small volume. Furthermore, the present method is readily adaptable to automation including high throughput screening systems.

In one embodiment, the present method is used to purify and concentrate a target pathogen from urine. The present method is able to separate the target pathogen from non-target molecules, and concentrate the target pathogen simultaneously.

In one embodiment, the present method is used to purify and concentrate a sexually transmitted infections-causing pathogen including but not limiting to *Chlamydia trachomatis* (CT), *Neisseria gonorrhoeae*, *Trichomonas vaginalis* and *Treponema pallidum* (syphilis) and Human Immunodeficiency Virus (HIV) from urine. In one embodiment, the present method is used to purify and concentrate sexually transmitted infections-causing pathogen in a subject biological sample including but are not limited to blood, plasma, serum, semen and other bodily fluids in where the pathogen may be present.

In one embodiment, during the HIV replication cycle, the newly released HIV virons go through a 'budding' process prior to shedding. Therefore, there are a significant amount of virus that are stuck to the eukaryotic host cells making them unavailable for detection by LFA, as the host cells are too big to flow through a LFA. In addition, to concentrate viral pathogens in general, the ATPS in the present invention aids the release of HIV virons from the host cells in a donated sample, thereby provides more target HIV pathogens for detection. It overall improves the sensitivity of the diagnosis. In one embodiment, ATPS with amphipathic phase forming molecules (such as a Triton 114 micellar ATPS) is used as these molecules are better equipped to disrupt the protein and lipid membrane connections between a budding HIV viron and the host cell.

In one embodiment, *Neisseria gonorrhoeae* have built in mechanisms to prevent immune response, and to prevent antibody binding. These mechanisms are largely due to membrane proteins such as pili, Opa proteins, and porins. Inhibition of antibody binding by these membrane proteins can cause an LFA diagnostic to fail by preventing binding of the colorimetric indicator (conjugate) to the target pathogen, or binding of the target pathogen to the test line prefixed with corresponding antibodies. The ATPS in the present invention does not only concentrate *Neisseria gonorrhoeae*, but alsos improve diagnostic performance by counteracting the prevention of antibody binding by the membrane proteins. In one embodiment, either micellar ATPS with added protein interfering agents (such as SDS), or Polymer/Salt ATPS with salts known to inhibit protein interaction through charge screening are used for this purpose.

In one embodiment of the present method, the target pathogen is retained on the ATPS while non-target materials are left in the liquid system (i.e., original sample plus any non-ATPS components).

Design of ATPS-Embedded Porous Material

In one embodiment, the present invention provides a porous material embedded with ATPS components. Various ATPS systems can be used in the present invention, including but are not limited to polymer-polymer (e.g. PEG-dextran), polymer-salt (e.g. PEG-salt), and micellar (e.g. Triton X-114). Porous material may be made of any suitable porous material which can absorb and transfer liquid. Suitable porous materials for this invention include but are not limited to fiberglass paper, cotton-based paper, other types of paper, polymer foams, cellulose foams, other types of foams, rayon fabric, cotton fabric, other types of fabric, wood, stones, and any other materials that can absorb and transfer liquid.

In one embodiment, the ATPS comprises a mixed phase solution comprising a first phase solution and a second phase solution, wherein components of said first phase solution and components of said second phase solution are embedded in said porous material at a concentration or a loading that is sufficient to undergo a phase separation as the mixed phase solution flows through the porous material.

In one embodiment, components of the first phase solution and/or the components of said second phase solution of the ATPS are embedded in the porous material and then dehydrated prior to the addition of a sample containing the target pathogen or bacterial to said porous material.

In one embodiment, components of the first phase solutions and/or the components of said second phase solution of the ATPS are combined with a sample containing the target pathogen or bacterial to create a mixture prior to the addition of said mixture to the porous material.

In one embodiment, some of the components of the first phase solution and/or the components of the second phase solution of the ATPS are embedded in the porous material and then dehydrated, while the remaining components of the first phase solutions and/or the components of the second phase solution are combined with a sample containing the target pathogen or bacterial to create a mixture prior to the addition of the mixture to the porous material.

In one embodiment, there is provided a two-component ATPS (aqueous two-phase system) within a porous material for the concentration of one or more target pathogen or bacterial s and/or the purification of a sample solution. The target pathogen or bacterial is in contact with the mixed phase solution comprising a first phase solution and a second phase solution, and partitions into the first phase solution, the second phase solution or the interface (or interphase) between the first phase solution and the second phase solution.

In one embodiment, there is provided a two-component ATPS (aqueous two-phase system) within a porous material for removing one or more contaminants from a sample, thereby obtains a purified sample of the target pathogen or bacterial (s). In one embodiment, the one or more contaminants are in contact with the mixed phase solution comprising a first phase solution and a second phase solution, and wherein the contaminants partitions into the first phase solution, the second phase solution, or the interface (or interphase) between the first phase solution and the second phase solution.

In one embodiment, the porous material and ATPS are selected so that the first phase solution flows through the porous matrix at a first rate and the second phase solution flows through the porous matrix at a second rate, wherein the first rate and the second rate are different.

In one embodiment, the porous material is commercially available or manufactured in-house.

Adjustment of Concentration Factors

In one embodiment, the relative amounts of ATPS components can be changed. The volume ratio of the two components of ATPS are controlled so as to concentrate the target pathogen or bacterial preferentially in one component.

In one embodiment, the present invention can reproducibly generate ATPS with extreme volume ratios in urine samples of different origins.

Figure 1A:
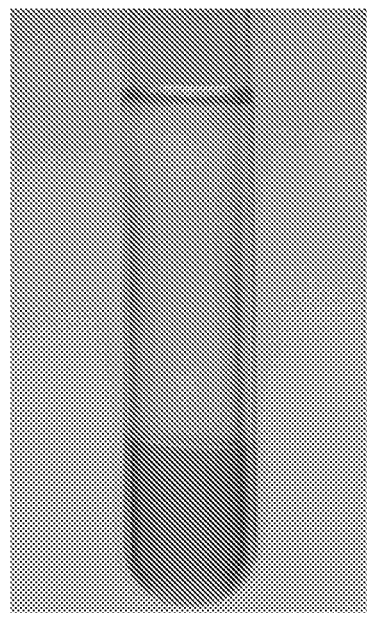
FIGS. 1A and 1B shows induction of phase separation and concentration by the addition of polymer and salt to a urine sample according to one embodiment of the present invention. Tube in FIG. 1A shows the phase separation after urine sample and ATPS components were mixed and the top/bottom phase volume ratio after separation is 2:1. The ATPS components underwent a phase separation and molecules in the urine sample partition in one of the two phases. Since the composition of ATPS components can be adjusted, the volume ratio of the first phase to the second phase can be changed from 2:1 to 9:1 as shown in FIG. 1A-1B. Target molecule in the urine sample can hence be concentrated in the phase of smaller volume and used/collected for subsequent analysis.
Figure 1B:
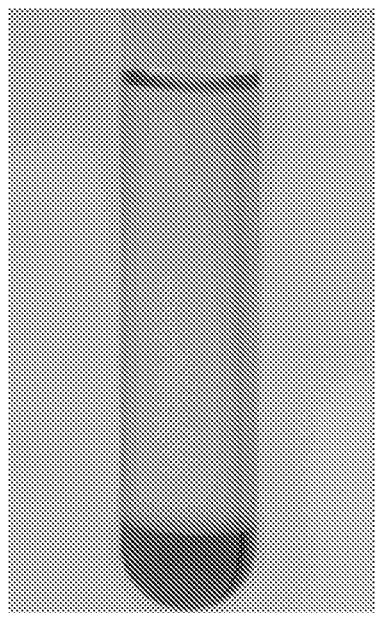

In one embodiment, the addition of polymer and salt to an aqueous solution can spontaneously drive phase separation with a defined volume ratio (FIGS. 1A and 1B). This phenomenon can be leveraged to concentrate a target molecule without the need for power, equipment, or training. In one embodiment, within a simple medium, such as a defined buffer, this is trivial to reproduce; however, given a complex medium like urine that has variable salt concentration (in addition to other interfering substances), it is more difficult to achieve a useful volume ratio with samples of different origins.

Figure 2:
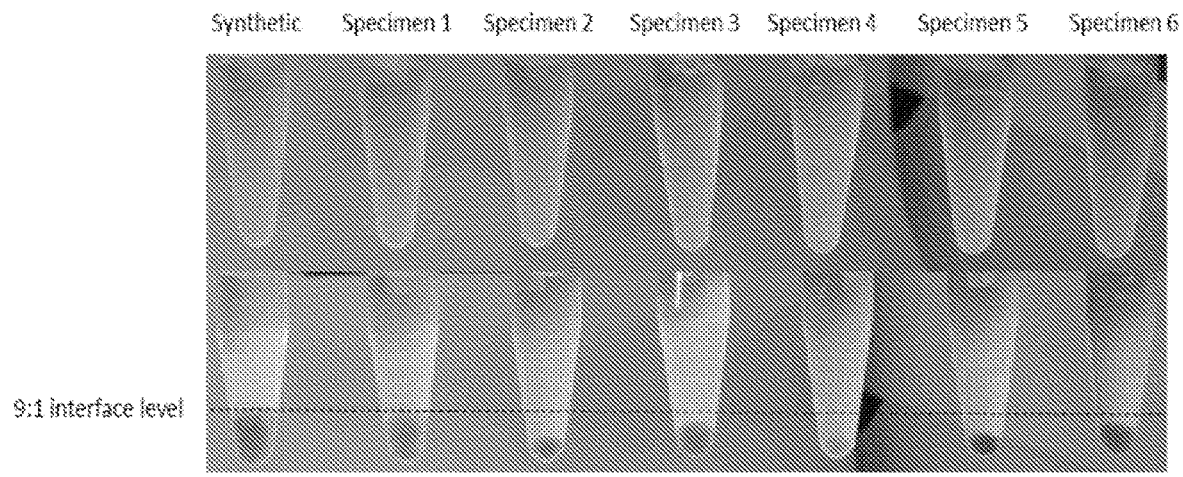
FIG. 2 shows phase separation in synthetic urine and urine specimens collected from different donors according to some embodiments of the present invention. The top panel shows the mixtures of phase solutions and sample prior to phase separation. The bottom panel shows the final state of the mixtures after phase separation. The concentrated phase containing the target analyte is indicated by a darker color as shown in the bottom. All tested urine samples achieved at least a 9:1 volume ratio, which is indicated by the dashed line.

FIG. 2 shows phase separation in synthetic urine and urine specimens collected from different donors. Top panel is the mixed phase solution prior to phase separation. Bottom panel is final state of phase separated solution with the concentrated phase indicated by a red/purple color. All urine samples tested achieved at least a 9:1 top to bottom volume ratio for the two separate phases, which is indicated by the dashed line.

In one embodiment, to integrate the ATPS components into the porous material, the ATPS components are solubilized in water (or appropriate buffer) and applied on the porous material in certain volume ratios. The porous materials were then placed in a lyophilizer to remove water, resulting in the ATPS components embedded directly on the porous material. Upon introduction of the sample to the porous materials, the ATPS components instantly undergo rehydration and thereby separate the molecules in the sample and concentrate the target biomarker at the front of the fluid flow without any external power or equipment to provide a driving force.

In one embodiment, the porous fiberglass paper is impregnated with ATPS which is made of polymer to polymer-based PEG-dextran. When a sample containing a plurality of biomolecules is poured onto the ATPS on the porous fiberglass paper, the impregnated porous fiberglass paper preferentially causes the biomolecules-containing ATPS components to flow ahead of the other ATPS components. Therefore, the targeted biomolecules is concentrated in the biomolecules-containing ATPS components at the front of the fluid flow.

In one embodiment, the porous fiberglass paper is pretreated with ATPS which is made of polymer to salt-based PEG-salt. When a sample containing a plurality of biomolecules is poured onto the ATPS on the porous fiberglass paper, the pretreated porous fiberglass paper preferentially causes the biomarker-containing ATPS components to flow ahead of the other ATPS components. Therefore, the targeted biomolecules is concentrated in the biomolecules-containing ATPS components and at the front of the fluid flow.

In one embodiment, the porous fiberglass paper is impregnated with ATPS which is made of micellar based surfactant-containing solutions. When a sample containing a plurality of biomolecules is poured onto the ATPS on the porous fiberglass paper, the impregnated porous fiberglass paper preferentially causes the biomolecules-containing ATPS components to flow ahead of the other ATPS components. Therefore, the targeted biomolecules is concentrated in the biomarker-containing ATPS components at the front of the fluid flow.

In one embodiment, there are various ATPS systems including but are not limited to polymer-polymer (e.g. PEG-dextran), polymer-salt (e.g. PEG-salt), and micellar (e.g. Triton X-114). The first and/or second component comprises a polymer. Polymer includes but is not limited to polyalkylene glycols, such as hydrophobically modified polyalkylene glycols, poly(oxyalkylene)polymers, poly(oxyalkylene)copolymers, such as hydrophobically modified poly(oxyalkylene)copolymers, polyvinyl pyrrolidone, polyvinyl alcohol, polyvinyl caprolactam, polyvinyl methylether, alkoxylated surfactants, alkoxylated starches, alkoxylated cellulose, alkyl hydroxyalkyl cellulose, silicone-modified polyethers, and poly N-isopropylacrylamide and copolymers thereof. In another embodiment, the first polymer comprises polyethylene glycol, polypropylene glycol, or dextran.

In one embodiment, the polymer concentration of the first component or second component is in the range of about 0.01% to about 90% by weight of the total weight of the aqueous solution (w/w). In various embodiments, the polymer solution is selected from a polymer solution that is about 0.01% w/w, about 0.05% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9%) w/w, about 0.95% w/w, or about 1% w/w. In some embodiments, the polymer solution is selected from polymer solution that is about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 46% w/w, about 47% w/w, about 48% w/w, about 49% w/w, and about 50% w/w.

In one embodiment, the first and/or second component comprises a salt, the salt includes but is not limited to kosmotropic salts, chaotropic salts, inorganic salts containing cations such as straight or branched trimethyl ammonium, triethyl ammonium, tripropyl ammonium, tributyl ammonium, tetramethyl ammonium, tetraethyl ammonium, tetrapropyl ammonium and tetrabutyl ammonium, and anions such as phosphates, sulphate, nitrate, chloride and hydrogen carbonate. In another embodiment, the salt is selected from the group consisting of NaCl, $Na_3PO_4$, $K_3PO_4$, $Na_2SO_4$, potassium citrate, $(NH_4)_2SO_4$, sodium citrate, sodium acetate and combinations thereof. Other salts, e.g. ammonium acetate, may also be used.

In one embodiment, the total salt concentration is in the range of 0.001 mM to 100 mM. A skilled person in the art will understand that the amount of salt needed to form an aqueous two-phase system will be influenced by molecular weight, concentration and physical status of the polymer.

In one embodiment, the first component and/or the second component in the ATPS comprises a solvent that is immiscible with water. In some embodiments, the solvent comprises a non-polar organic solvent. In some embodiments, the solvent comprises an oil. In some embodiments, the solvent is selected from pentane, cyclopentane, benzene, 1,4-dioxane, diethyl ether, dichloromethane, chloroform, toluene and hexane.

In one embodiment, the first component and/or second component in the ATPS comprises a micellar solution. In some embodiments, the micellar solution comprises a non-ionic surfactant. In some embodiments, the micellar solution comprises a detergent. In some embodiments, the micellar solution comprises Triton-X. In some embodiments, the micellar solution comprises a polymer similar to Triton-X, such as Igepal CA-630 and Nonidet P-40. In some embodiments, the micellar solution consists essentially of Triton-X.

In one embodiment, the first component in the ATPS comprises a micellar solution and the second component in the liquid phase comprises a polymer. In one embodiment, the second component in the liquid phase comprises a micellar solution and the first component in the liquid phase comprises a polymer. In one embodiment, the first component in the liquid phase comprises a micellar solution and the second component in the liquid phase comprises a salt. In one embodiment, the second component in the liquid phase comprises a micellar solution and the first component comprises a salt. In one embodiment, the micellar solution is a Triton-X solution. In one embodiment, the first component comprises a first polymer and the second component comprises a second polymer. In one embodiment, the first/second polymer is selected from polyethylene glycol and dextran. In one embodiment, the first component comprises a polymer and the second component comprises a salt. In one embodiment, the second component comprises a polymer and the first component comprises a salt. In some embodiments, the first component comprises polyethylene glycol and the second component comprises potassium phosphate. In some embodiments, the second component comprises polyethylene glycol and the first component comprises potassium phosphate. In one embodiment, the first component comprises a salt and the second component comprises a salt. In one embodiment, the first component comprises a kosmotropic salt and the second component comprises a chaotropic salt. In some embodiments, the second component comprises a kosmotropic salt and the first component comprises a chaotropic salt.

Improvement of Diagnostic Procedures Using the Lateral-Flow Immunoassay (LFA)

Urine samples obtained by the present method can be subject to detection or analysis using the Lateral-Flow Immunoassay (LFA) for diagnosing sexually transmitted infections.

Lateral flow immunoassay (LFA) methods and devices have been described extensively. See, e.g., Gordon and Pugh, U.S. Pat. No. 4,956,302; H. Buck, et al., WO 90/06511; T. Wang, U.S. Pat. No. 6,764,825; W. Brown, et al., U.S. Pat. No. 5,008,080; Kuo and Meritt, U.S. Pat. No.

6,183,972, EP 00987551A3. Such assays involve the detection and determination of an analyte substance that is a member of a specific binding pair consisting of a ligand and a receptor. The ligand and the receptor are related in that the receptor specifically binds to the ligand, being capable of distinguishing a specific ligand or ligands from other sample constituents having similar characteristics Immunological assays involving reactions between antibodies and antigens are one such example of a specific binding assay. Other examples include DNA and RNA hybridization reactions and binding reactions involving hormones and other biological receptors.

Figure 4:
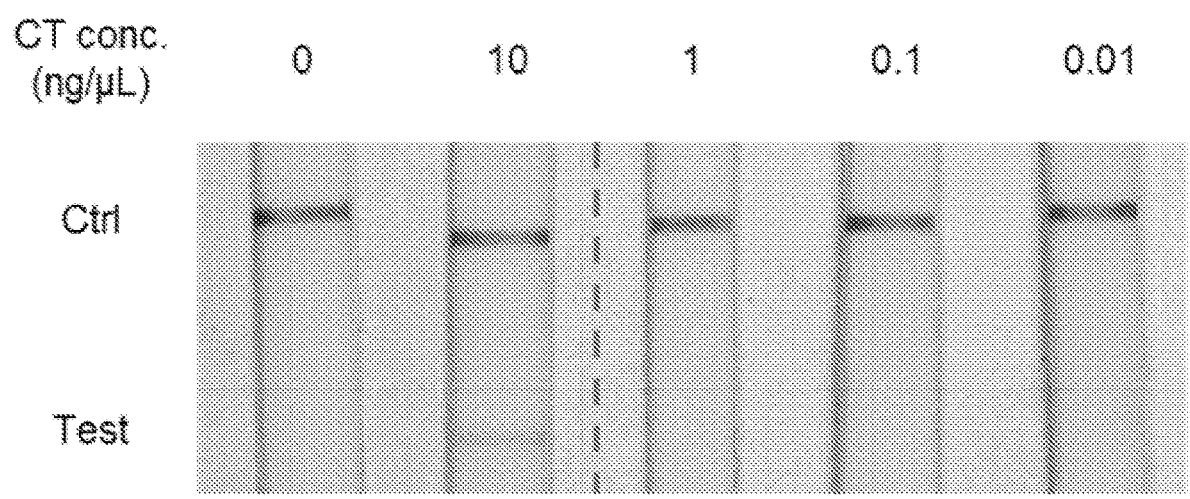
FIG. 4 shows results of a series of LFA tests using urine samples spiked with CT at the indicated concentrations according to one embodiment of the present invention. The presence of a test line ("test") denotes a positive result. The presence of a control line ("ctrl") denotes a valid test. The vertical dash line represents the limit of detection of this series of LFA tests.
Figure 5:
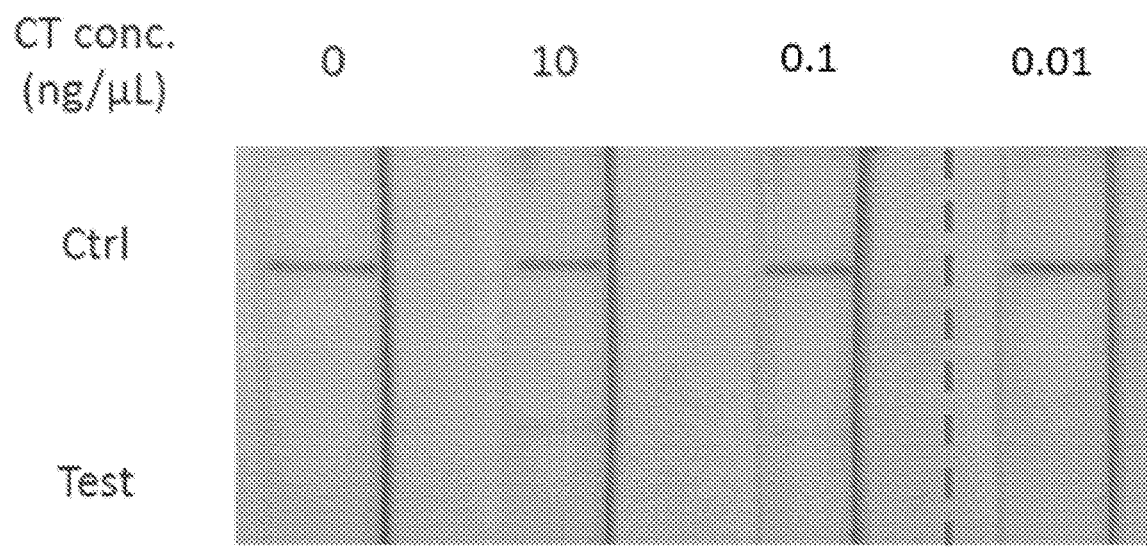
FIG. 5 shows the results of a series of ATPS-LFA tests using urine samples spiked with CT at the indicated concentrations according to one embodiment of the present invention. The presence of a test line ("test") denotes a positive result. The presence of a control line ("ctrl") denotes a valid test. The vertical dash line represents the limit of detection of this series of ATPS-LFA tests.

In one embodiment, analyte and/or analytes-containing solution obtained by the present invention can be analyzed by a lateral flow assay (LFA). LFA has a number of desirable characteristics including their ease of use and broad applicability to a variety of analytes. However, LFA is generally only capable of providing qualitative results due to its detection limitation. For example, the detection limit of LFA on pathogen (*Chlamydia trachomatis*) is 10 ng/ul. In the present invention wherein impurities (urea and proteins in urine sample) are first removed from the urine sample, the detection limit of LFA on *Chlamydia trachomatis* can be improved to as low as 0.1 ng/ul which is a 100-fold enhancement as shown in FIGS. 4 and 5. Together with the improved concentration fold by 100-fold, the present invention is suited for providing quantitative result in a broader range.

In one embodiment, the present invention adapts gold nanoparticles (GNs) to work with urine-based ATPS.

In one embodiment, antibodies specific to the target molecules are decorated on the surfaces of GNs to form gold nanoprobes (GNPs), which act as the colorimetric indicators for the detection assay. The colloidal stability of GNs is pivotal as unstable GNs could lead to aggregation, which will affect flow and binding, and ultimately reduce the sensitivity and functionality of the assay.

In one embodiment, the present invention provides a method of screening antibodies for their compatibility with urine samples.

In one embodiment, the present invention uses urine-based ATPS described herein to identify antibodies for the detection of *Chlamydia trachomatis* (CT). In one embodiment, nine commercially available antibodies that target different antigens on CT (Table 1) were tested pairwise (both conjugated to GNs and immobilized on the paper microfluidic strip), the results of which are shown in Table 2. Many pairs either did not bind to CT strongly enough, resulting in a false negative, or displayed nonspecific binding, resulting in a false positive. Six promising antibody pairs were identified. Using one of the best pairs from these experiments, a LFA test was developed to detect CT which is compatible with urine sample (FIG. 4) and was able to achieve a limit of detection at 10 ng/μL.

TABLE 1

Nine commercially available antibodies for detecting *Chlamydia trachomatis*

| Antibodies | Isotype | Supplier |
|---|---|---|
| A | IgG | Abcam, ab20723 |
| B | IgG | Abcam, ab21211 |
| C | IgG | Abcam, ab21048 |
| D | IgG | Abcam, ab20387 |
| E | IgG | Abcam, ab106853 |
| F | IgM | Quest, 86632 |
| G | IgG | Sigma, SDL8333 |

TABLE 1-continued

Nine commercially available antibodies for detecting *Chlamydia trachomatis*

| Antibodies | Isotype | Supplier |
|---|---|---|
| H | IgM | Sigma, SDL8334 |
| I | IgA | Sigma, SDL8332 |

In one embodiment, the present invention integrates ATPS with a urine-based LFA test, which can greatly improve the sensitivity of detection.

TABLE 2

Summary of antibody screening efforts to identify promising pairs for further evaluation in urine and ATPS conditions

| | GN | | | | | | | | |
|---|---|---|---|---|---|---|---|---|---|
| M | Ab-A | Ab-B | Ab-C | Ab-D | Ab-E | Ab-F | Ab-G | Ab-H | Ab-I |
| Ab-A | *** | ** | * | ** | *** | * | * | ** | ** |
| Ab-B | ** | ** | * | ** | *** | * | * | ** | * |
| Ab-C | ** | ** | ** | ** | ** | * | * | * | * |
| Ab-D | * | ** | * | *** | *** | * | * | ** | * |
| Ab-E | ** | ** | ** | ** | *** | * | * | NT | * |
| Ab-F | * | NT | * | * | * | * | * | * | * |
| Ab-G | * | NT | * | NT | * | * | NT | NT | NT |
| Ab-H | * | NT | * | NT | * | * | * | * | * |
| Ab-I | * | NT | * | NT | * | * | NT | NT | NT |

* no or very faint test lines observed;
** nonspecific binding;
*** promising antibody pair for evaluation;
NT, not tested.
Ab: antibody;
M: membrane;
GN: gold nanoparticle.

In one embodiment, with the established urine-based ATPS and LFA, the limit of detection of LFA in this purified medium (urine) was improved. Combining the present ATPS and LFA resulted in a 100-fold improvement in the limit of detection to 0.1 ng/μL (FIG. 5). This represented the first time an improvement in the limit of detection of CT in an actual biological medium.

In one embodiment, the combined ATPS-LFA testing approach provided by this invention is found to achieve a better performance than a current FDA-approved predicate QuickVue test for diagnosing CT infection in remnant clinical patient urine samples.

TABLE 3

Comparison of different CT detection methods

| Sample | Type | NAAT | Quick Vue | Phase's LFA | Phase's LFA ATPS |
|---|---|---|---|---|---|
| 1 | Neat | + | − | + | + |
| 2 | Neat | + | − | − | + |
| 3 | Neat | + | − | − | + |
| 4 | Neat | + | − | − | + |
| 5 | Neat | + | − | − | + |
| 6 | Neat | + | − | − | + |
| 7 | Frozen | + | − | − | + |
| 8 | Frozen | + | − | − | + |
| 9 | Frozen | + | − | − | + |
| 10 | Frozen | + | − | − | + |
| 11 | Frozen | + | − | − | − |
| 12 | Frozen | + | − | − | − |
| 13 | Frozen | + | − | − | + |
| 14 | Frozen | + | − | − | + |

TABLE 3-continued

Comparison of different CT detection methods

| Sample | Type | NAAT | Quick Vue | Phase's LFA | Phase's LFA ATPS |
|---|---|---|---|---|---|
| 15 | Frozen | + | − | − | + |
| 16 | Frozen | + | − | − | + |

Figure 6:
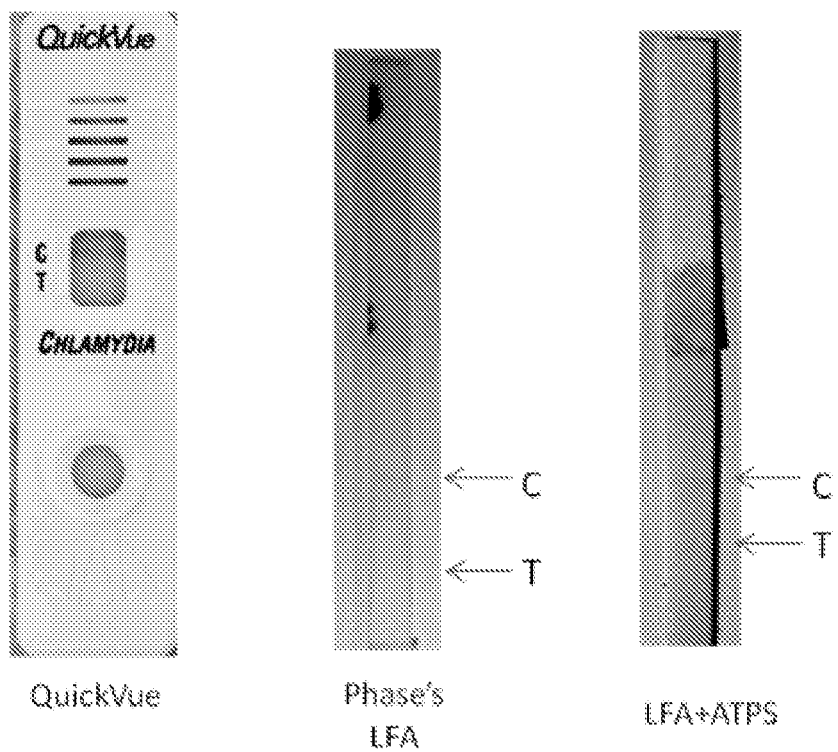
FIG. 6 is an example of the representative results (sample #4, Table 2) of the head-to-head comparison among QuickVue, the present LFA module, and the present LFA-ATPS module. The presence of the test line (T) indicates a true positive result. Only the present LFA+ATPS module had a visible test line indicating a true positive result.

In one embodiment, building off of the improvement using urine samples that contained spiked quantities of CT, these quantities were verified in fact physiologically relevant. Using remnant clinical urine specimens, the urine-based LFA alone exhibits a poor sensitivity, consistent with what can be obtained with the QuickVue test for samples in urine. However, when the urine-based LFA was integrated with the present ATPS, the sensitivity is significantly improved, recognizing 87.5% (14/16) CT+ urine samples with a positive result. (Table 3). These results are extremely prominent and promising, showing the present invention can be reliably used in clinical settings to detect or diagnose CT based on actual clinical patient samples. FIG. 6 shows one example of the head-to-head performance comparison study described above.

Table 3 summarizes a performance comparison study between FDA approved QuickVue test, the present LFA test, and the present LFA-ATPS test in the detection of CT in remnant clinical urine samples. All samples were confirmed to be CT-positive by a nucleic acid amplification test (NAAT). In contrast to the frozen samples, neat samples were freshly collected ones.

In one embodiment, since the actual urine samples may contain interfering substances that may affect the detection, a preliminary screen of substances that could be contained within urine was performed (Table 4). These interference substances are suggested by FDA guidelines for CT assay development. It is found that none of the substances interfered with the results of our tests at the limit of detection.

The indicated substances were spiked into the urine sample to verify that the accuracy of the test was not affected by the presence of these substances.

TABLE 4

Interference results for the present LFA test

| Substance Added | Concentration | Negative Test | Positive Test (at LoD) |
|---|---|---|---|
| None | N/A | − | + |
| pH 4.5 PBS | N/A | − | + |
| Human whole blood | 5% v/v | − | + |
| Human serum | 10% v/v | − | + |
| Bilirubin | 20 mg/dL | − | + |
| Acetaminophen | 10 mg/dL | − | + |
| Ibuprofen | 10 mg/dL | − | + |
| Salicylic acid | 0.5% w/v | − | + |

In one embodiment, the present invention provides a single-step process based on an optimized 3-D paper well which fully integrates ATPS with LFA.

In one embodiment, in order to minimize user interaction, a solution where all components of the ATPS are fully contained within a paper device was developed so that the test can be conducted naturally and immediately after the sample is collected and loaded to the present device. FIG. 9 shows one embodiment of the present device adapting a 3D paper architecture in which the 3D paper well and LFA are linked together by tape. In another embodiment, the 3D paper well, LFA, membranes and other components are contained in a housing.

In one embodiment, the present device is optimized by using paper materials which promote phase separation of a mixed phase solution. Various paper materials were tested and one paper material was found to produce a strong concentrated leading front, while other papers either promoted tortuous flow or reversed the order of flow of the two phases (i.e., polymer-rich phase without the target flows first).

Figure 7:
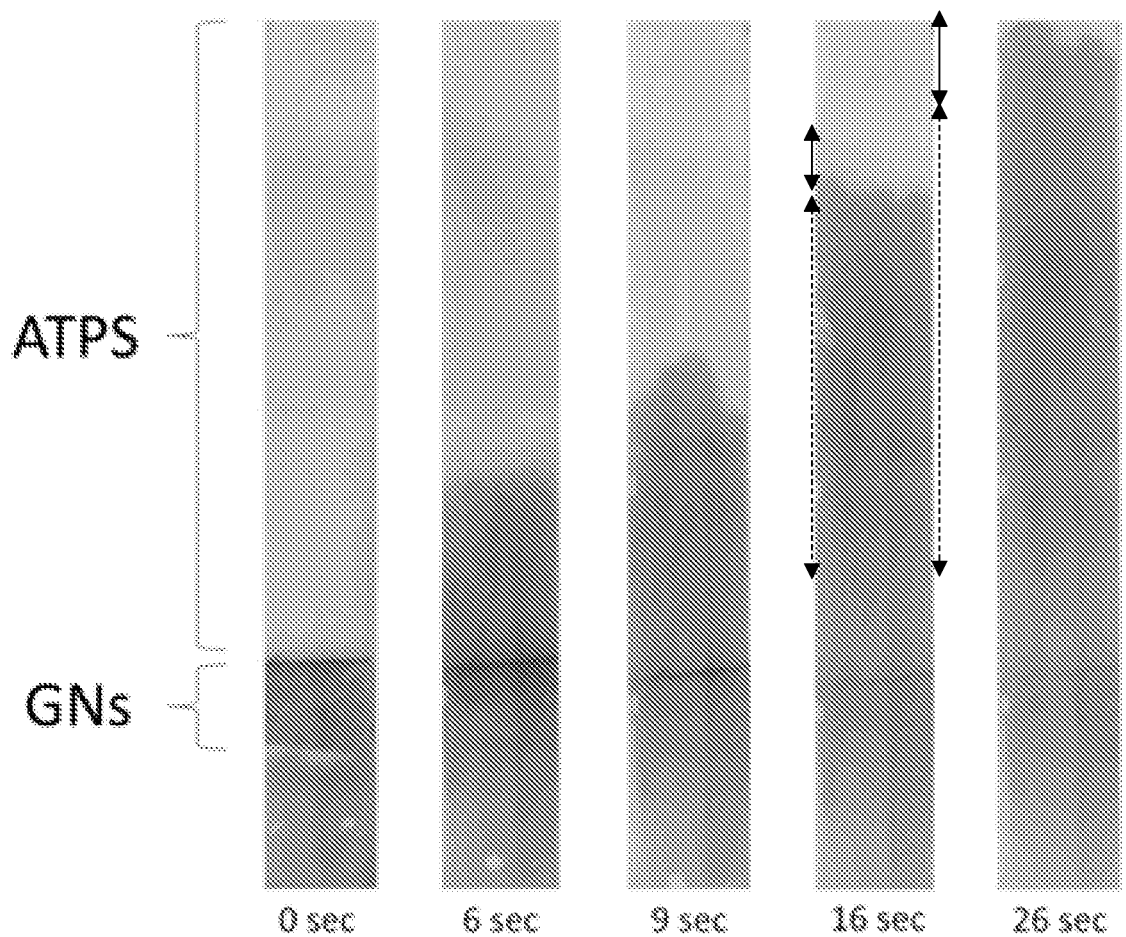
FIG. 7 shows the spontaneous phase separation of a solution using a paper strip with dehydrated ATPS components according to one embodiment of the present invention. Initially, as illustrated in the first column of the upper panel, the gold nanoparticles (GNs) were rehydrated by a solution containing a blue dye. The dye and GNs were well mixed as the solution rehydrates the ATPS components. The solution then underwent a phase separation, resulting in a clear purple leading front (indicated by arrow) while the blue dye (indicated by dashed-arrow) was held back.

In one embodiment, various methods of applying the ATPS components to the paper were considered. The ability of liquid to flow on strips of a particular type of paper (Paper A, which had been treated with the present proprietary ATPS components) was tested. It was found that certain methods were superior when considering their effects on wicking time. Wicking time is an important parameter in the assay as it could affect the overall level of non-specific binding and overall assay time. A short wick time will enable a rapid result with minimal undesired nonspecific binding. Using an optimal method for applying ATPS components to the paper, it is confirmed that urine containing no additives can be separated spontaneously all within the paper (FIG. 7).

In one embodiment, the present invention also provides a device comprising ATPS as a concentration module linked with a purifying unit and a lateral flow immunoassay (LFA) component as a detection module. In one embodiment, the detection module is housed in a plastic housing with a viewing window. As a sample solution wicks up the device and ATPS components undergo phase separation, the analytes are concentrated in the leading front. Concentrated analytes are then detected by the LFA module by generating visual test results. In one embodiment, the test result is shown to an end user directly by observation. In one embodiment, the test result is shown to an end user indirectly, e.g., with assistance of UV lamp. In one embodiment, the test result is shown to an end user in a form of quantitative manner, including but not limited to, a concentration of the target analyte on a reader.

In one embodiment, by incorporating dehydrated ATPS components with LFA, the present invention provides a one-step method and device that are capable of a sensitive and accurate detection of pathogens such as CT.

Figure 8:
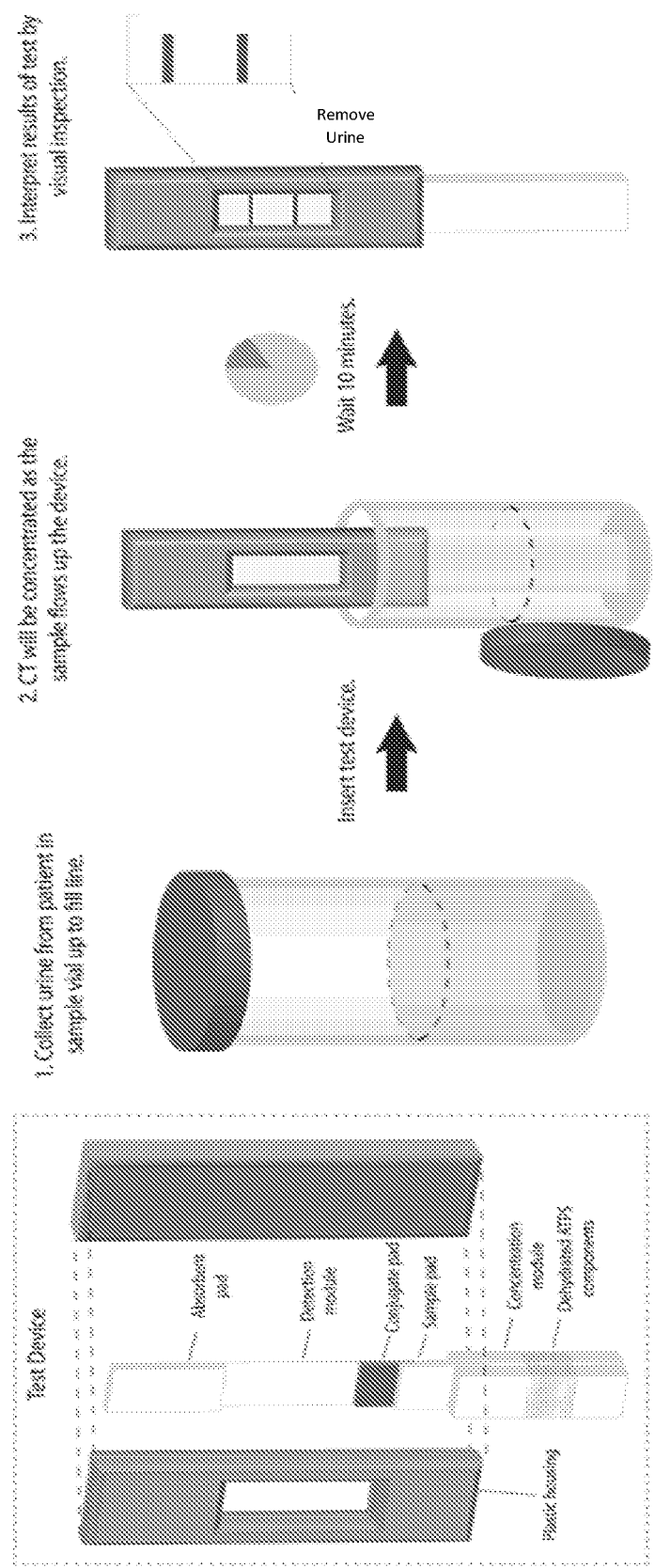
FIG. 8 is a schematic diagram of the present device according to one embodiment of the present invention. The fully integrated ATPS and LFA test strip concentrates the CT bacteria present in urine, allowing rapid and accurate diagnosis within 10 minutes with minimal user interaction.
Figure 10:
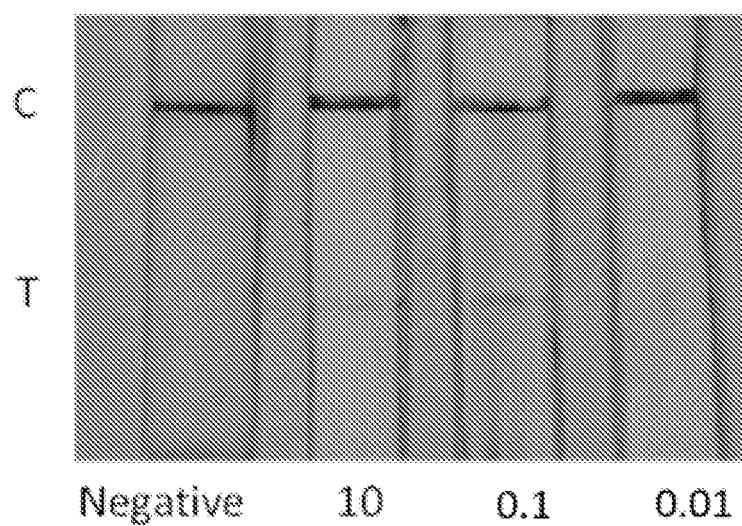
FIG. 10 shows the results of the present one-step device. The presence of a test line (T) denotes a positive result. The presence of a control line (C) denotes a valid test.

FIG. 8 shows one embodiment of the present invention, where the device is incredibly simple to use for clinicians and patients. In one embodiment, with just a single step, the present device can detect CT within 10 minutes. In another embodiment, the present device is built by applying all the achieved findings (FIG. 9). In one embodiment, the present invention demonstrates a detection limit of 0.1 ng/µL in spiked synthetic urine samples (FIG. 10), and expects to achieve a similar detection limit in real urine samples.

In one embodiment, the present invention discloses a system for the detection and quantification of a pathogen associated with a sexually transmitted disease or infection in a specimen from a subject, the system comprises:
(a) a purifying unit for removing interfering molecules that interfere with detection of a said pathogen,
(b) a concentrating module for concentrating said pathogen,
(c) a conjugate pad comprising labelled biorecognition molecules, each of which comprising a label and a biorecognition molecule, and
(d) a detecting module comprising a membrane covered with a control line and one or more test lines, the concentrating module comprises a porous material precoated with components of an Aqueous Two-Phase System (ATPS), and when a sample solution comprising said pathogen flows through said porous material, two separated phases are formed, the pathogen is concentrated in one of the two separated phases, and positive results on said control line and one or more test lines indicate the presence of said pathogen in said subject.

In one embodiment, the purifying unit comprises a purifying agent that forms a precipitate by reacting with said interfering molecules, the precipitate is retained in the purifying unit and does not migrate with liquid flow, or the precipitate does not interfere with the detection of said pathogen.

In one embodiment, the purifying agent includes but is not limited to citric acid, lactic acid, acetic acid, and activated carbon.

In one embodiment, the pathogen includes but is not limited to *Chlamydia trachomatis, Neisseria gonorrhoeae, Trichomonas vaginalis* and *Treponema pallidum* (syphilis), and Human Immunodeficiency Virus.

In one embodiment, the porous material includes but is not limited to fiber-glass paper, cotton-based paper, single-layer matrix paper, and polyolefin foam pad.

In one embodiment, the ATPS components include but are not limited to polymers, salts, and surfactants.

In one embodiment, the polymer(s) includes but is not limited to polyalkylene glycols, poly(oxyalkylene)polymers, poly(oxyalkylene)copolymers, polyvinyl pyrrolidone, polyvinyl alcohol, polyvinyl caprolactam, polyvinyl methylether, alkoxylated surfactants, alkoxylated starches, alkoxylated cellulose, alkyl hydroxyalkyl cellulose, silicone-modified polyethers, poly N-isopropylacrylamide, polyethylene glycol, polypropylene glycol, and dextran.

In one embodiment, the salts include but are not limited to kosmotropic salts, chaotropic salts, inorganic salts having a cation of trimethyl ammonium, triethyl ammonium, tripropyl ammonium, tributyl ammonium, tetramethyl ammonium, tetraethyl ammonium, tetrapropyl ammonium or tetrabutyl ammonium, and an anion of phosphate, sulphate, nitrate, chloride or hydrogen carbonate, NaCl, $Na_3PO_4$, $K_3PO_4$, $Na_2SO_4$, potassium citrate, $(NH_4)_2SO_4$, sodium citrate, sodium acetate, ammonium acetate, and any combinations thereof.

In one embodiment, the surfactants include but are not limited to nonionic surfactants, detergents, Triton-X, Igepal CA-630, and Nonidet P-40.

In one embodiment, one or more test lines are pre-fixed with one or more antibodies or antigens, and one or more antibodies or antigens specifically bind with the pathogen or a complex comprising said pathogen.

In one embodiment, the system detects *Chlamydia trachomatis* at a concentration as low as 0.1 ng/ul.

In one embodiment, the present invention discloses a method of detecting a pathogen associated with a sexually transmitted disease or infection in a subject, the method comprises:
 (a) obtaining a specimen comprising the pathogen from the subject;
 (b) removing interfering molecules that interfere with detection of the pathogen by reacting the interfering molecules with a purifying agent, thereby obtaining a sample solution substantially free from the interfering molecules;
 (c) concentrating the pathogen in the sample solution by a concentrating module, the concentrating module comprises a porous material precoated with components of an Aqueous Two-Phase System (ATPS), where when the sample solution flows through the porous material, two separated phases are formed, and the pathogen is concentrated in one of the two separated phases, thereby obtaining a concentrated solution;
 (d) allowing the concentrated solution to migrate to a conjugate pad comprising labeled biorecognition molecules, each of which comprising a label and a biorecognition molecule, where the pathogen is bound by the biorecognition molecules, thereby obtaining a complex between the labeled biorecognition molecules and the pathogen, and
 (e) detecting the complex on a testing module comprising a membrane covered with a control line and one or more test lines,
where positive results at said control line and one or more test lines indicate the presence of said pathogen in said subject.

In one embodiment, the purifying agent forms a precipitate by reacting with the interfering molecules, wherein the precipitate does not migrate with liquid flow, or the precipitate does not interfere with the detection of the pathogen.

In one embodiment, the purifying agent includes but is not limited to citric acid, lactic acid, acetic acid, and activated carbon.

In one embodiment, the pathogen includes but is not limited to *Chlamydia trachomatis, Neisseria gonorrhoeae, Trichomonas vaginalis* and *Treponema pallidum* (syphilis), and Human Immunodeficiency Virus.

In one embodiment, the porous material includes but is not limited to fiberglass paper, cotton-based paper, single-layer matrix paper, and polyolefin foam pad.

In one embodiment, the ATPS components include but are not limited to polymers, salts, and surfactants.

In one embodiment, the polymers include but are not limited to polyalkylene glycols, poly(oxyalkylene)polymers, poly(oxyalkylene)copolymers, polyvinyl pyrrolidone, polyvinyl alcohol, polyvinyl caprolactam, polyvinyl methylether, alkoxylated surfactants, alkoxylated starches, alkoxylated cellulose, alkyl hydroxyalkyl cellulose, silicone-modified polyethers, poly N-isopropylacrylamide, polyethylene glycol, polypropylene glycol, and dextran.

In one embodiment, the salts include but are not limited to kosmotropic salts, chaotropic salts, inorganic salts having a cation of trimethyl ammonium, triethyl ammonium, tripropyl ammonium, tributyl ammonium, tetramethyl ammonium, tetraethyl ammonium, tetrapropyl ammonium or tetrabutyl ammonium, and an anion of phosphate, sulphate, nitrate, chloride or hydrogen carbonate, NaCl, $Na_3PO_4$, $K_3PO_4$, $Na_2SO_4$, potassium citrate, $(NH_4)_2SO_4$, sodium citrate, sodium acetate, ammonium acetate, and any combinations thereof.

In one embodiment, the surfactants include but are not limited to nonionic surfactants, detergents, Triton-X, Igepal CA-630, and Nonidet P-40.

In one embodiment, the one or more test lines are pre-fixed with one or more antibodies or antigens, wherein the one or more antibodies or antigens specifically bind with the pathogen or the complex comprising the pathogen.

In one embodiment, the method detects *Chlamydia trachomatis* at concentrations as low as 0.1 ng/ul.

This invention will be better understood by reference to the examples which follow. However, one skilled in the art will readily appreciate that the examples provided are merely for illustrative purposes and are not meant to limit the scope of the invention which is defined by the claims following thereafter.

EXAMPLES

Example 1—Removal of Urea and Protein from Urine 0.5 ml of urine was mixed with 0.5 ml of citric acid (25% w/v in water) and the mixture was vortexed to mix thoroughly and allowed to sit for 5 min at room temperature. This was followed by centrifugation at 15,000 rpm for 2 min. The supernatant was collected. Sodium carbonate was added to neutralize the supernatant until pH is about 6.2. The supernatant can then be concentrated by lyophilizer or ATPS system as demonstrated in FIGS. 1A and 1B if needed.

Existence of urea in the urine sample or supernatant can be detected by the following method:
Take 0.1 ml urine sample in a measuring cylinder from the urine sample bottle.
Take a test tube and pour the urine sample into the test tube.
Using a dropper, take sodium hypobromite solution.
Add few drops of sodium hypobromide solution to the urine sample.
Brisk effervescence of nitrogen shown in the test tube indicates presence of urea in the urine.

In this example, no brisk effervescence was observed, suggesting that all the urea had been successfully removed from the urine sample.

Existence of protein in the supernatant can be detected by UV at 280 nm. In this example, no reading at 280 nm was observed at UV at 280 nm for the supernatant, suggesting that all the protein molecules had been successfully removed from urine.

Example 2—Use of ATPS to Concentrate the Urine Supernatant

The supernatant prepared according to the method in Example 1 (1 ml) was added to 1 ml ATPS components comprising 25% (w/w) PEG and 7.2% (w/w) potassium phosphate. The mixture was vortexed to mix thoroughly and allowed the phase to separate. About 10 min later, the mixture phase separated. The volume ratio of top phase to the bottom phase was around 9:1, and the target molecule (shown in purple) was concentrated in the bottom phase with a 5-fold concentration in comparison to the concentration in the supernatant.

Example 3—Detection of Chlamydia trachomatis (CT) by LFA in Patient Samples

Preparation of sample pad for LFA: Fiberglass porous paper sheets were cut into 0.5 cm×4 cm rectangles. The formulated ATPS components, 20% (w/w) PEG and 18.5% (w/w) potassium phosphate were pipetted onto the fiberglass porous paper. The above porous papers with ATPS were then dried in a lyophilizer for 2 hours first. Pieces were then stacked as 3D paper well (eight strips per stack) and were further cut into a tapered shape so that it forms a 45-degree angle at one end. The tapered papers were assembled together so that the direction of flow is vertical to the horizontal line and the taper is 'pointing up' (as shown in the first embodiment from the left in FIG. 3). The tapering is also enabled by the 45 degree angled cuts in each layer of the porous material.

PEG solution (in DI H$_2$O) was added to each porous material. 50 µl of a Tris-buffered solution containing 2% bovine serum albumin (BSA), and 0.1% PEG, 20 mM Tris pH 7.5 respectively) was added immediately adjacent to the first solution. The ATPS within porous papers were then placed in an indicator-containing (colloidal gold) buffer solution in PBS (overall pH 7.4), resulting in capillary action-mediated flow.

Preparation of LFA test strip: 1) Anti-*Chlamydia trachomatis* antibody (IgG) at a concentration of 1 mg/mL (supplied by Abcam ab20723), and 2) Protein (Bovine Serum Albumin, BSA) at a concentration of 0.2 mg/ml were added on the test strip. Colloidal gold nanoparticles were conjugated to the anti-*Chlamydia trachomatis* antibody as directed by manufacturer instructions. This conjugate was then dried onto the conjugating pad material using a lyophilizer. The absorbent pad consisted of untreated paper.

The LFA test strip was integrated with sample pad, i.e., the porous device/component with the dehydrated ATPS components and the phase separation behavior modifying agent. The porous device/component and the LFA component were placed into an appropriate housing such that the components were held in place.

Detection using LFA: The fiberglass porous paper dehydrated with ATPS components were dipped into urine prepared in Example 2 which was in a PBS buffer solution at pH 7.4. Urine without purification/treatment was used for comparison. After the urine solution flowed through the porous material and through the LFA test for 5 min, another 5 min was needed to develop the test results. The detection limit was observation. The result is summarized in Table 5 below:

TABLE 5

Detection limit of *Chlamydia trachomatis*

| Sample | Detection limit |
| --- | --- |
| Urine without treatment | 10 ng/ul |
| Urine treated with citric acid | 0.1 ng/ul |

Example 4—Detecting Human Immunodeficiency Virus (HIV) by LFA in Patient Samples Preparation of sample pad for LFA: Fiberglass porous paper sheets were cut into 0.5 cm×4 cm rectangles. The formulated ATPS components, 18% (w/w) PEG and 15% (w/w) potassium phosphate were pipetted onto the fiberglass porous paper. The above porous papers with ATPS were then dried in a lyophilizer for 2 hours first. Pieces were then stacked as 3D paper well (eight strips per stack) and were further cut into a tapered shape so that it forms a 45-degree angle with the point. Assemble the tapered paper together so that the direction of flow is vertical and the taper is 'pointing up (same as Example 3).

PEG solution (in DI H$_2$O) was first added to each porous material. 50 µl of a Tris-buffered solution containing 2% bovine serum albumin (BSA), and 0.1% PEG, 20 mM Tris pH 7.5 respectively) was added immediately after the addition of the first solution. The ATPS within porous papers were then placed in an indicator-containing (colloidal gold) buffer solution in PBS (overall pH 7.4), resulting in capillary action-mediated flow.

Preparation of LFA test strip: 1) Anti-HIV antibody (IgG) at a concentration of 1 mg/mL (supplied by Abcam ab20723), and 2) Protein (Bovine Serum Albumin, BSA) at a concentration of 0.2 mg/ml were added on the test strip. Colloidal gold nanoparticles were conjugated to the anti-HIV antibody as directed by manufacturer instructions. This conjugate was then dried onto the conjugating pad material using a lyophilizer. The absorbent pad consisted of untreated paper.

The LFA test strip was integrated with sample pad, i.e., the porous device/component with the dehydrated ATPS components and the phase separation behavior modifying agent. The porous device/component and the LFA component are placed into an appropriate housing such that the components are held in place.

Detection using LFA: The fiberglass porous paper dehydrated with ATPS components were dipped into urine prepared in urea-free and protein-free urine samples which was in a PBS buffer solution at pH 7.4. Urine without purification/treatment was used for comparison. After the urine solution flowed through the porous material and through the LFA test for 5 min, another 5 min was needed to develop the test results. The detection limit was observation. The result is summarized in Table 6 below:

TABLE 6 detection limit of *Chlamydia trachomatis*

| Sample | Sensitivity |
|---|---|
| Urine without treatment | 55% |
| Urine treated with citric acid | 95% |

What is claimed is:

1. A system for the detection and quantification of a pathogen associated with a sexually transmitted disease or infection in a specimen from a subject, said system comprising:
    (a) a purifying unit for removing interfering molecules that interfere with detection of said pathogen,
    (b) a concentrating module for concentrating said pathogen,
    (c) a conjugate pad comprising labelled biorecognition molecules, each of which comprising a label and a biorecognition molecule, and
    (d) a detecting module comprising a membrane covered with a control line and one or more test lines,
wherein said concentrating module comprises a porous material precoated with components of an Aqueous Two-Phase System (ATPS), wherein when a sample solution comprising said pathogen flows through said porous material, two separated phases are formed, wherein the pathogen is concentrated in one of the two separated phases, and wherein positive results on said control line and one or more test lines indicate the presence of said pathogen in said subject, wherein said purifying unit comprises a purifying agent that forms a precipitate by reacting with said interfering molecules, and wherein said purifying agent is selected from the group consisting of citric acid, lactic acid, acetic acid, and activated carbon.

2. The system of claim 1, wherein said precipitate is retained in the purifying unit and does not migrate with liquid flow, or said precipitate does not interfere with the detection of said pathogen.

3. The system of claim 1, wherein said pathogen is selected from the group consisting of *Chlamydia trachomatis*, *Neisseria gonorrhoeae*, *Trichomonas vaginalis* and *Treponema pallidum* (syphilis), and Human Immunodeficiency Virus.

4. The system of claim 1, wherein the porous material is selected from the group consisting of fiber-glass paper, cotton-based paper, single-layer matrix paper, and polyolefin foam pad.

5. The system of claim 1, wherein said ATPS components are selected from the group consisting of polymers, salts, and surfactants.

6. The system of claim 5, wherein said polymers are selected from the group consisting of polyalkylene glycols, poly(oxyalkylene)polymers, poly(oxyalkylene)copolymers, polyvinyl pyrrolidone, polyvinyl alcohol, polyvinyl caprolactam, polyvinyl methylether, alkoxylated surfactants, alkoxylated starches, alkoxylated cellulose, alkyl hydroxyalkyl cellulose, silicone-modified poly ethers, poly N-isopropylacrylamide, polyethylene glycol, polypropylene glycol, and dextran.

7. The system of claim 5, wherein said salts are selected from the group consisting of kosmotropic salts, chaotropic salts, inorganic salts having a cation of trimethyl ammonium, triethyl ammonium, tripropyl ammonium, tributyl ammonium, tetramethyl ammonium, tetraethyl ammonium, tetrapropyl ammonium or tetrabutyl ammonium, and an anion of phosphate, sulphate, nitrate, chloride or hydrogen carbonate, NaCl, $Na_3PO_4$, $K_3PO_4$, $Na_2SO_4$, potassium citrate, $(NH_4)_2SO_4$, sodium citrate, sodium acetate, ammonium acetate, and any combinations thereof.

8. The system of claim 5, wherein said surfactants are selected from the group consisting of nonionic surfactants, detergents, Triton-X, Igepal CA-630, and Nonidet P-40.

9. The system of claim 1, wherein said one or more test lines are pre-fixed with one or more antibodies or antigens, wherein said one or more antibodies or antigens specifically bind with the pathogen or a complex comprising said pathogen.

10. A method of detecting a pathogen associated with a sexually transmitted disease or infection in a subject, said method comprising:
    (f) obtaining a specimen comprising said pathogen from said subject;
    (g) removing interfering molecules that interfere with detection of said pathogen by reacting said interfering molecules with a purifying agent, thereby obtaining a sample solution substantially free from said interfering molecules;
    (h) concentrating said pathogen in said sample solution by a concentrating module, said concentrating module comprises a porous material precoated with components of an Aqueous Two-Phase System (ATPS), wherein when said sample solution flows through said porous material, two separated phases are formed, wherein the pathogen is concentrated in one of the two separated phases, thereby obtaining a concentrated solution;
    (i) allowing said concentrated solution to migrate to a conjugate pad comprising labeled biorecognition molecules, each of which comprising a label and a biorecognition molecule, wherein said pathogen is bound by said biorecognition molecules, thereby obtaining a complex between said labeled biorecognition molecules and said pathogen, and
    (j) detecting said complex on a testing module comprising a membrane covered with a control line and one or more test lines,
wherein positive results at said control line and one or more test lines indicate the presence of said pathogen in said subject, wherein said purifying agent forms a precipitate by reacting with said interfering molecules, and wherein said purifying agent is selected from the group consisting of citric acid, lactic acid, acetic acid, and activated carbon.

11. The method of claim 10, wherein said precipitate does not migrate with liquid flow, or said precipitate does not interfere with the detection of said pathogen.

12. The method of claim 10, wherein said pathogen is selected from the group consisting of *Chlamydia trachomatis, Neisseria gonorrhoeae, Trichomonas vaginalis* and *Treponema pallidum* (syphilis), and Human Immunodeficiency Virus.

13. The method of claim 10, wherein the porous material is selected from the group consisting of fiberglass paper, cotton-based paper, single-layer matrix paper, and polyolefin foam pad.

14. The method of claim 10, wherein said ATPS components are selected from the group consisting of polymers, salts, and surfactants.

15. The method of claim 14, wherein said polymers are selected from the group consisting of polyalkylene glycols, poly(oxyalkylene)polymers, poly(oxyalkylene)copolymers, polyvinyl pyrrolidone, polyvinyl alcohol, polyvinyl caprolactam, polyvinyl methylether, alkoxylated surfactants, alkoxylated starches, alkoxylated cellulose, alkyl hydroxyalkyl cellulose, silicone-modified poly ethers, poly N-isopropylacrylamide, polyethylene glycol, polypropylene glycol, and dextran.

16. The method of claim 14, wherein said salts are selected from the group consisting of kosmotropic salts, chaotropic salts, inorganic salts having a cation of trimethyl ammonium, triethyl ammonium, tripropyl ammonium, tributyl ammonium, tetramethyl ammonium, tetraethyl ammonium, tetrapropyl ammonium or tetrabutyl ammonium, and an anion of phosphate, sulphate, nitrate, chloride or hydrogen carbonate, NaCl, $Na_3PO_4$, $K_3PO_4$, $Na_2SO_4$, potassium citrate, $(NH_4)_2SO_4$, sodium citrate, sodium acetate, ammonium acetate, and any combinations thereof.

17. The method of claim 14, wherein said surfactants are selected from the group consisting of nonionic surfactants, detergents, Triton-X, Igepal CA-630, and Nonidet P-40.

18. The method of claim 10, wherein said one or more test lines are pre-fixed with one or more antibodies or antigens, wherein said one or more antibodies or antigens specifically bind with the pathogen or said complex comprising said pathogen, wherein said method detects *Chlamydia trachomatis* at concentrations as low as 0.1 ng/ul.

19. The system of claim 1, wherein said system detects *Chlamydia trachomatis* at a concentration as low as 0.1 ng/ul.

20. The system of claim 1, wherein said specimen is a urine sample.

21. The system of claim 1, wherein said purifying agent is citric acid.

* * * * *